(12) United States Patent
Esteller et al.

(10) Patent No.: US 12,257,435 B2
(45) Date of Patent: Mar. 25, 2025

(54) ASSESSMENT AND ADJUSTMENT OF TIME-VARYING PULSE PATTERNS IN A SPINAL CORD STIMULATOR SYSTEM

(71) Applicant: Boston Scientific Neuromodulation Corporation, Valencia, CA (US)

(72) Inventors: Rosana Esteller, Santa Clarita, CA (US); Jessica Block, Los Angeles, CA (US); Changfang Zhu, Valencia, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 425 days.

(21) Appl. No.: 17/753,866

(22) PCT Filed: Sep. 24, 2020

(86) PCT No.: PCT/US2020/052520
§ 371 (c)(1),
(2) Date: Mar. 16, 2022

(87) PCT Pub. No.: WO2021/080727
PCT Pub. Date: Apr. 29, 2021

(65) Prior Publication Data
US 2022/0347479 A1 Nov. 3, 2022

Related U.S. Application Data

(60) Provisional application No. 62/923,818, filed on Oct. 21, 2019.

(51) Int. Cl.
*A61N 1/36* (2006.01)
*A61N 1/05* (2006.01)
*A61N 1/372* (2006.01)

(52) U.S. Cl.
CPC ....... *A61N 1/36071* (2013.01); *A61N 1/0551* (2013.01); *A61N 1/36132* (2013.01);
(Continued)

(58) Field of Classification Search
CPC .............. A61N 1/0551; A61N 1/36071; A61N 1/36132; A61N 1/36178; A61N 1/36189; A61N 1/37247
See application file for complete search history.

(56) References Cited

U.S. PATENT DOCUMENTS 6,516,227 B1   2/2003 Meadows et al.
9,155,892 B2  10/2015 Parker et al.
(Continued)

FOREIGN PATENT DOCUMENTS

WO   2015013398 A1   1/2015
WO   2015/063127 A1  5/2015
(Continued)

OTHER PUBLICATIONS

International Search Report and Written Opinion regarding corresponding PCT Application No. PCT/US2020/052520, mailed Dec. 16, 2020.
(Continued)

*Primary Examiner* — George Manuel
(74) *Attorney, Agent, or Firm* — Lewis & Reese, PLLC

(57) ABSTRACT

Methods, system, and computer-implementable algorithms are disclosed for determining time-varying pulses for a patient having an implantable stimulator device (ISD). At least one time-invariant tonic stimulation pulse parameter (e.g., amplitude, pulse width, or frequency) is modified by a modulation function to produce time-varying pulses (TVPs), and one or more measurements are taken to determine the effectiveness of the TVP. The measurements may be objective and taken from the patient, and/or subjective and
(Continued)

determined based on feedback from the patient. In one example, objective measurements may comprise one or more features determined from an electrospinogram (ESG) signal detected by the ISD, which may include evoked compound action potentials The one or more measurements are used to determine a score for the TVP, which is useful in selecting a best TVP for use with the patient, or for adjusting the modulation function applied to the tonic stimulation parameters.

19 Claims, 10 Drawing Sheets

(52) U.S. Cl.
CPC ...... *A61N 1/36178* (2013.01); *A61N 1/36189* (2013.01); *A61N 1/37247* (2013.01)

(56) References Cited

U.S. PATENT DOCUMENTS

| | | | |
|---|---|---|---|
| 9,265,431 | B2 | 2/2016 | Hincapie Ordonez et al. |
| 9,386,934 | B2 | 7/2016 | Parker et al. |
| 9,782,592 | B2 | 10/2017 | Lee |
| 9,872,990 | B2 | 1/2018 | Parker et al. |
| 9,974,455 | B2 | 5/2018 | Parker et al. |
| 10,406,368 | B2 | 9/2019 | Hershey et al. |
| 2011/0313489 | A1 | 12/2011 | Erickson |
| 2013/0289665 | A1 | 10/2013 | Marnfeldt et al. |
| 2014/0194772 | A1 | 7/2014 | Single et al. |
| 2014/0236042 | A1 | 8/2014 | Parker et al. |
| 2014/0236257 | A1 | 8/2014 | Parker et al. |
| 2014/0277267 | A1 | 9/2014 | Vansickle et al. |
| 2014/0296737 | A1 | 10/2014 | Parker et al. |
| 2014/0364920 | A1 | 12/2014 | Doan et al. |
| 2015/0282725 | A1 | 10/2015 | Single |
| 2015/0313487 | A1 | 11/2015 | Single et al. |
| 2016/0121119 | A1 | 5/2016 | Alataris et al. |
| 2016/0287126 | A1 | 10/2016 | Parker et al. |
| 2016/0287182 | A1 | 10/2016 | Single et al. |
| 2017/0049345 | A1 | 2/2017 | Single |
| 2017/0071490 | A1 | 3/2017 | Parker et al. |
| 2017/0216587 | A1 | 8/2017 | Parker |
| 2017/0266447 | A1 | 9/2017 | Zhu |
| 2017/0361101 | A1 | 12/2017 | Single |
| 2018/0110987 | A1 | 4/2018 | Parker |
| 2018/0110991 | A1 | 4/2018 | Molnar et al. |
| 2018/0117335 | A1 | 5/2018 | Parker et al. |
| 2018/0228391 | A1 | 8/2018 | Parker et al. |
| 2018/0256052 | A1 | 9/2018 | Parker et al. |
| 2018/0369573 | A1* | 12/2018 | Cholette ............ A61N 1/36139 |
| 2019/0099602 | A1 | 4/2019 | Esteller et al. |
| 2019/0175915 | A1 | 6/2019 | Brill et al. |
| 2019/0209844 | A1 | 7/2019 | Esteller et al. |
| 2019/0275331 | A1 | 9/2019 | Zhu |
| 2019/0290900 | A1 | 9/2019 | Esteller et al. |
| 2019/0299006 | A1 | 10/2019 | Marnfeldt |
| 2020/0046980 | A1 | 2/2020 | Moffitt et al. |
| 2020/0147393 | A1 | 5/2020 | Zhang et al. |
| 2020/0230410 | A1 | 7/2020 | Zhang et al. |
| 2020/0305744 | A1 | 10/2020 | Weerakoon et al. |
| 2020/0305745 | A1 | 10/2020 | Wagenbach et al. |
| 2020/0346019 | A1 | 11/2020 | Weiss et al. |

FOREIGN PATENT DOCUMENTS

| | | |
|---|---|---|
| WO | 2017/100866 | 6/2017 |
| WO | 2017/173493 | 10/2017 |
| WO | 2019/157559 | 8/2019 |
| WO | 2020/251899 | 12/2020 |

OTHER PUBLICATIONS

First Office Action regarding corresponding Chinese Patent Application No. 202080074015.6, mailed Jun. 28, 2024.

* cited by examiner

Modulation function 150

Modulation shape:

⟨triangular wave⟩ Triangular
⟨sinusoid wave⟩ Sinusoid
⟨ramped wave⟩ Ramped
⟨stair step wave⟩ Stair step
⟨random wave⟩ Random 162 — ☒ (Triangular selected)

Stim parameter to be modulated:

163 — ☒ Amplitude (A)
☐ Pulse width (PW)
☐ Frequency (F)

Modulation parameters:

164

Amin: 2.5 mA
Amax: 4.0 mA
Amid: 3.25 mA
A Spread: 23%
A modulation frequency ($F_M$): 0.5 Hz PWmin: ___
PWmax: ___
PWmid: ___
PW Spread: ___
PW modulation frequency ($F_M$): ___

Fmin: ___
Fmax: ___
Fmid: ___
F Spread: ___
F modulation frequency ($F_M$): ___

GUI 160

*Figure 7B*

*Score:*

Sx for TVPx = (w1 * OMax) + (w2 * OMbx) + ... + (w3 * SMax) + (w4 * SMbx) + ...

Objective measurement:
E.g., normalized spread of ECAP AUC

| TVP2 | 0.4 |
| TVP1 | 0.10 |
| TVP4 | 0.12 |
| TVP3 | 0.35 |

Subjective measurements (SM):
E.g., pain score | Perception threshold (Pth)

| 3 | 6.0 mA |
| 5 | 4.2 mA |
| 4 | 5.0 mA |
| 6 | 7.2 mA |

Score may comprise a single measurement if only one is used.

| Score |
| --- |
| -0.35 |
| -0.57 |
| -0.58 |
| -0.67 |

Assume w1 = 1; w2 = -0.05; w3 = -0.1

*Figure 10*

ASSESSMENT AND ADJUSTMENT OF TIME-VARYING PULSE PATTERNS IN A SPINAL CORD STIMULATOR SYSTEM

FIELD OF THE INVENTION

This application relates to Implantable Medical Devices (IMDs), and more specifically to techniques for determining optimal time-varying stimulation pulses for a given patient.

INTRODUCTION

Implantable neurostimulator devices are devices that generate and deliver electrical stimuli to body nerves and tissues for the therapy of various biological disorders, such as pacemakers to treat cardiac arrhythmia, defibrillators to treat cardiac fibrillation, cochlear stimulators to treat deafness, retinal stimulators to treat blindness, muscle stimulators to produce coordinated limb movement, spinal cord stimulators to treat chronic pain, cortical and deep brain stimulators to treat motor and psychological disorders, and other neural stimulators to treat urinary incontinence, sleep apnea, shoulder subluxation, etc. The description that follows will generally focus on the use of the invention within a spinal cord stimulation (SCS) system, such as that disclosed in U.S. Pat. No. 6,516,227. However, the present invention may find applicability with any implantable neurostimulator device system.

An SCS system typically includes an Implantable Pulse Generator (IPG) 10 shown in FIG. 1. The IPG 10 includes a biocompatible conductive device case 12 that holds the IPG's circuitry and a battery 14 for providing power for the IPG to function. The IPG 10 is coupled to tissue-stimulating electrodes 16 via one or more electrode leads that form an electrode array 17. For example, one or more percutaneous leads 15 can be used having ring-shaped or split-ring electrodes 16 carried on a flexible body 18. In another example, a paddle lead 19 provides electrodes 16 positioned on one of its generally flat surfaces. Lead wires 20 within the leads are coupled to proximal contacts 21, which are insertable into lead connectors 22 fixed in a header 23 on the IPG 10, which header can comprise an epoxy for example. Once inserted, the proximal contacts 21 connect to header contacts 24 within the lead connectors 22, which are in turn coupled by feedthrough pins 25 through a case feedthrough 26 to stimulation circuitry 28 within the case 12, which stimulation circuitry 28 is described below.

In the illustrated IPG 10, there are thirty-two electrodes (E1-E32), split between four percutaneous leads 15, or contained on a single paddle lead 19, and thus the header 23 may include a 2×2 array of eight-electrode lead connectors 22. However, the type and number of leads, and the number of electrodes, in an IPG is application specific and therefore can vary. The conductive case 12 can also comprise an electrode (Ec), and thus the electrode array 17 can include one or more leads and the case electrode 12. In a SCS application, the electrode lead(s) are typically implanted in the spinal column proximate to the dura in a patient's spinal cord, preferably spanning left and right of the patient's spinal column. The proximal contacts 21 are then tunneled through the patient's tissue to a distant location such as the buttocks where the IPG case 12 is implanted, where they are coupled to the lead connectors 22. In other IPG examples designed for implantation directly at a site requiring stimulation, the IPG can be lead-less, having electrodes 16 instead appearing on the body of the IPG 10 for contacting the patient's tissue. The IPG lead(s) can be integrated with and permanently connected to the IPG 10 in other solutions. The goal of SCS therapy is to provide electrical stimulation from the electrodes 16 to alleviate a patient's symptoms, such as chronic back pain.

IPG 10 can include an antenna 27a allowing it to communicate bi-directionally with a number of external devices discussed subsequently. Antenna 27a as shown comprises a conductive coil within the case 12, although the coil antenna 27a can also appear in the header 23. When antenna 27a is configured as a coil, communication with external devices (FIG. 5) preferably occurs using near-field magnetic induction. IPG 10 may also include a Radio-Frequency (RF) antenna 27b. RF antenna 27b is shown within the header 23, but it may also be within the case 12. RF antenna 27b may comprise a patch, slot, or wire, and may operate as a monopole or dipole. RF antenna 27b preferably communicates using far-field electromagnetic waves, and may operate in accordance with any number of known RF communication standards, such as Bluetooth, Zigbee, MICS, and the like. The IPG 10 can also include an accelerometer 31 able to detect the orientation of the IPG 10 in the patient, which can be useful to determining a patient's posture (e.g., standing, prone, supine, etc.).

Stimulation in IPG 10 is typically provided by a sequence of waveforms (e.g., pulses) each of which may include a number of phases such as 30a and 30b, as shown in the example of FIG. 2A. Stimulation parameters typically include amplitude (current A, although a voltage amplitude V can also be used); frequency (F) (or period T, where T=1/F); pulse width (PW) of the phases of the waveform such as 30a and 30b; the electrodes 16 selected to provide the stimulation; and the polarity of such selected electrodes, i.e., whether they act as anodes that source current to the tissue or cathodes that sink current from the tissue. These and possibly other stimulation parameters taken together comprise a stimulation program that the stimulation circuitry 28 in the IPG 10 can execute to provide therapeutic stimulation to a patient.

In the example of FIG. 2A, electrode E1 has been selected as an anode (during first phase 30a), and thus sources a positive current of amplitude +A to the tissue. Electrode E2 has been selected as a cathode (again during first phases 30a), and thus sinks a corresponding negative current of amplitude −A from the tissue. However, more than one electrode may be selected to act as an anode at a given time, and more than one electrode may be selected to act as a cathode at a given time. The case electrode Ec may also be selected as an anode or cathode by itself or along with one or more lead-based electrodes.

IPG 10 as mentioned includes stimulation circuitry 28 to form prescribed stimulation at a patient's tissue. FIG. 3 shows an example of stimulation circuitry 28, which includes one or more current sources $40_i$ and one or more current sinks 41. The sources and sinks $40_i$ and $42_i$ can comprise Digital-to-Analog converters (DACs), and may be referred to as PDACs $40_i$ and NDACs $42_i$ in accordance with the Positive (sourced, anodic) and Negative (sunk, cathodic) currents they respectively issue. In the example shown, a NDAC/PDAC $40_i/42_i$ pair is dedicated (hardwired) to a particular electrode node ei 39. Each electrode node ei 39 is connected to an electrode Ei 16 via a DC-blocking capacitor Ci 38, for the reasons explained below. PDACs $40_i$ and NDACs $42_i$ can also comprise voltage sources.

Proper control of the PDACs $40_i$ and NDACs $42_i$ allows any of the electrodes 16 and the case electrode Ec 12 to act as anodes or cathodes to create a current through a patient's tissue, R, hopefully with good therapeutic effect. In the example shown, and consistent with the first phase 30a of FIG. 2A, electrode E1 has been selected as an anode electrode to source current +A to the tissue R and electrode E2 has been selected as a cathode electrode to sink current −A from the tissue R. Thus PDAC 401 and NDAC 422 are activated and digitally programmed to produce the desired current, A, with the correct timing (e.g., in accordance with the prescribed frequency F and pulse width PW). Power for the stimulation circuitry 28 is provided by a compliance voltage VH, as described in further detail in U.S. Patent Application Publication 2013/0289665.

Other stimulation circuitries 28 can also be used in the IPG 10. In an example not shown, a switching matrix can intervene between the one or more PDACs $40_i$ and the electrode nodes ei 39, and between the one or more NDACs $42_i$ and the electrode nodes. Switching matrices allows one or more of the PDACs or one or more of the NDACs to be connected to one or more electrode nodes at a given time. Various examples of stimulation circuitries can be found in U.S. Pat. Nos. 6,181,969, 8,606,362, 8,620,436, U.S. Patent Application Publications 2018/0071520 and 2019/0083796.

Much of the stimulation circuitry 28 of FIG. 3, including the PDACs $40_i$ and NDACs $42_i$, the switch matrices (if present), and the electrode nodes ei 39 can be integrated on one or more Application Specific Integrated Circuits (ASICs), as described in U.S. Patent Application Publications 2012/0095529, 2012/0092031, 2012/0095519, 2018/0071516, and 2018/0071513, which are incorporated herein by reference in their entireties. As explained in these references, ASIC(s) may also contain other circuitry useful in the IPG 10, such as telemetry circuitry (for interfacing off chip with telemetry antennas 27a and/or 27b), circuitry for generating the compliance voltage VH, various measurement circuits, etc.

Also shown in FIG. 3 are DC-blocking capacitors Ci 38 placed in series in the electrode current paths between each of the electrode nodes ei 39 and the electrodes Ei 16 (including the case electrode Ec 12). The DC-blocking capacitors 38 act as a safety measure to prevent DC current injection into the patient, as could occur for example if there is a circuit fault in the stimulation circuitry 28. The DC-blocking capacitors 38 are typically provided off-chip (off of the ASIC(s)), and instead may be provided in or on a circuit board in the IPG 10 used to integrate its various components, as explained in U.S. Patent Application Publication 2015/0157861.

Referring again to FIG. 2A, the stimulation waveforms as shown are biphasic, with each waveform comprising a first phase 30a followed thereafter by a second phase 30b of opposite polarity. (Although not shown, an interphase period during which no active current is driven may intervene between the phases 30a and 30b). Both of the phases 30a and 30b are actively driven by the stimulation circuitry 28 by causing relevant PDACs $40_i$ and NDACs $42_i$ to drive the prescribed currents. Biphasic waveforms are useful to actively recover any charge that might be stored on capacitive elements in the current path, such as on the DC-blocking capacitors 38. To recover all charge by the end of the second phase 30b of each waveform (Vc1=Vc2=0V), the first and second phases 30a and 30b are charged balanced at each electrode, with the first phase 30a providing a charge of +Q (+A*PW) and the second phase 30b providing a charge of −Q (−A*PW) at electrode E1, and with the first phase 30a providing a charge of −Q and the second phase 30b providing a charge of +Q at the electrode E2. In the example shown, such charge balancing is achieved by using the same phase width (PW) and the same amplitude (|A|) for each of the opposite-polarity phases 30a and 30b. However, the phases 30a and 30b may also be charged balance at each electrode if the product of the amplitude and pulse width of the two phases 30a and 30b are equal, or if the area under each of the phases (their integrals) is equal, as is known. Although not shown, the waveforms may also be monophasic, meaning that there is only one active phase, i.e., only first phase 30a or second phase 30b.

FIG. 3 shows that stimulation circuitry 28 can include passive recovery circuitry, which is described further in U.S. Patent Application Publications 2018/0071527 and 2018/0140831. Specifically, passive recovery switches $41_i$ may be attached to each of the electrode nodes ei 39, and are used to passively recover any charge remaining on the DC-blocking capacitors Ci 38 after issuance of a last pulse phase—i.e., after the second phase 30b if a biphasic pulses are used, or after the sole pulse phase if monophasic pulses are used. Note that passive charge recovery is illustrated as small exponentially-decaying curves during 30c in FIG. 2A due to the R-C nature of the circuit, and this current may be positive or negative depending on whether phase 30a or 30b has a predominance of charge at a given electrode. These exponentially-decaying curves would be larger were monophasic pulses used.

FIG. 4 shows an external trial stimulation environment that may precede implantation of an IPG 10 in a patient. During external trial stimulation, stimulation can be tried on a prospective implant patient without going so far as to implant the IPG 10. Instead, one or more trial electrode arrays 17' (e.g., one or more trial percutaneous leads 15 or trial paddle leads 19) are implanted in the patient's tissue at a target location 52, such as within the spinal column as explained earlier. The proximal ends of the trial electrode array(s) 17' exit an incision 54 and are connected to an External Trial Stimulator (ETS) 50. The ETS 50 generally mimics operation of the IPG 10, and thus can provide stimulation to the patient's tissue via its stimulation circuitry 58, which may be equivalent or identical to stimulation circuitry 28 in the IPG 10. The ETS 50 is generally worn externally by the patient for a short while (e.g., two weeks), which allows the patient and his clinician to experiment with different stimulation parameters to hopefully find a stimulation program that alleviates the patient's symptoms (e.g., pain). If external trial stimulation proves successful, the trial electrode array(s) 17' are explanted, and a full IPG 10 and a permanent electrode array 17 (e.g., one or more percutaneous 15 or paddle 19 leads) are implanted as described above; if unsuccessful, the trial electrode array(s) 17' are simply explanted. Like the IPG 10, the ETS 50 can include one or more antennas to enable bi-directional communications with external devices such as those shown in FIG. 5. Such antennas can include a near-field magnetic-induction coil antenna 56a, and/or a far-field RF antenna 56b, as described earlier. ETS 50 may also include a battery (not shown) for operational power.

FIG. 5 shows various external devices that can wirelessly communicate data with the IPG 10 and the ETS 50, including a patient hand-held external controller 60, and a clinician programmer 70. Both of devices 60 and 70 can be used to wirelessly transmit a stimulation program to the IPG 10 or ETS 50—that is, to program their stimulation circuitries 28 and 58 to produce stimulation with a desired amplitude and timing, and at selected electrodes. Both devices 60 and 70 may also be used to adjust one or more stimulation parameters of a stimulation program that the IPG 10 or ETS 50 is currently executing. Devices 60 and 70 may also wirelessly receive information from the IPG 10 or ETS 50, such as various status information, etc.

External controller 60 can be as described in U.S. Patent Application Publication 2015/0080982 for example, and may comprise a controller dedicated to work with the IPG 10 or ETS 50. External controller 60 may also comprise a general purpose mobile electronics device such as a mobile phone which has been programmed with a Medical Device Application (MDA) allowing it to work as a wireless controller for the IPG 10 or ETS 50, as described in U.S. Patent Application Publication 2015/0231402. External controller 60 includes a Graphical User Interface (GUI), preferably including means for entering commands (e.g., buttons or selectable graphical icons) and a display 62, thus allowing the patient the ability to control the IPG 10 or ETS 50. The external controller 60's GUI enables a patient to adjust stimulation parameters, although it may have limited functionality when compared to the more-powerful clinician programmer 70, described shortly. The external controller 60 can have one or more antennas capable of communicating with the IPG 10 and ETS 50. For example, the external controller 60 can have a near-field magnetic-induction coil antenna 64*a* capable of wirelessly communicating with the coil antenna 27*a* or 56*a* in the IPG 10 or ETS 50. The external controller 60 can also have a far-field RF antenna 64*b* capable of wirelessly communicating with the RF antenna 27*b* or 56*b* in the IPG 10 or ETS 50.

Clinician programmer 70 is described further in U.S. Patent Application Publication 2015/0360038, and can comprise a computing device 72, such as a desktop, laptop, or notebook computer, a tablet, a mobile smart phone, a Personal Data Assistant (PDA)-type mobile computing device, etc. In FIG. 5, computing device 72 is shown as a laptop computer that includes typical computer user interface means such as a screen 74, a mouse, a keyboard, speakers, a stylus, a printer, etc., not all of which are shown for convenience. Also shown in FIG. 5 are accessory devices for the clinician programmer 70 that are usually specific to its operation as a stimulation controller, such as a communication "wand" 76 coupleable to suitable ports on the computing device 72, such as USB ports 79 for example.

The antenna used in the clinician programmer 70 to communicate with the IPG 10 or ETS 50 can depend on the type of antennas included in those devices. If the patient's IPG 10 or ETS 50 includes a coil antenna 27*a* or 56*a*, wand 76 can likewise include a coil antenna 80*a* to establish near-field magnetic-induction communications at small distances. In this instance, the wand 76 may be affixed in close proximity to the patient, such as by placing the wand 76 in a belt or holster wearable by the patient and proximate to the patient's IPG 10 or ETS 50. If the IPG 10 or ETS 50 includes an RF antenna 27*b* or 56*b*, the wand 76, the computing device 72, or both, can likewise include an RF antenna 80*b* to establish communication with the IPG 10 or ETS 50 at larger distances. The clinician programmer 70 can also communicate with other devices and networks, such as the Internet, either wirelessly or via a wired link provided at an Ethernet or network port.

To program stimulation programs or parameters for the IPG 10 or ETS 50, the clinician interfaces with a clinician programmer GUI 82 provided on the display 74 of the computing device 72. As one skilled in the art understands, the GUI 82 can be rendered by execution of clinician programmer software 84 stored in the computing device 72, which software may be stored in the device's non-volatile memory 86. Execution of the clinician programmer software 84 in the computing device 72 can be facilitated by controller circuitry 88 such as one or more microprocessors, microcomputers, FPGAs, DSPs, other digital logic structures, etc., which are capable of executing programs in a computing device, and which may comprise their own memories. In one example, controller circuitry 88 may comprise an i5 processor manufactured by Intel Corp., as described at https://www.intel.com/content/www/us/en/products/processors/core/i5-processors.html. Such controller circuitry 88, in addition to executing the clinician programmer software 84 and rendering the GUI 82, can also enable communications via antennas 80*a* or 80*b* to communicate stimulation parameters chosen through the GUI 82 to the patient's IPG 10 or ETS 50.

The GUI of the external controller 60 may provide similar functionality because the external controller 60 can include the same or similar hardware and software programming as the clinician programmer 70. For example, the external controller 60 includes controller circuitry 66 similar to the controller circuitry 88 in the clinician programmer 70, and may similarly be programmed with external controller software stored in device memory.

SUMMARY

A method for determining stimulation for a patient having an implantable stimulator device is disclosed, which may comprise: (a) applying different modulation functions to time-invariant pulse parameters to create a plurality of different time-varying pulse waveforms, wherein each of the modulation functions modulates at least one of the time-invariant pulse parameters; (b) applying each of the time-varying pulse waveforms to the patient via the implantable stimulator device; (c) obtaining at least one measurement for each of the applied time-varying pulse waveforms; and (d) selecting one or more of the time-varying pulse waveforms for the patient based at least in part on the at least one measurements.

In one example, the method further comprises as an initial step determining the time-invariant pulse parameters for use with the patient. In one example, the at least one measurement obtained for each of the applied time-varying pulse waveforms is indicative of the effectiveness of that time-varying pulse waveform for the patient. In one example, the time-invariant pulse parameters comprise a pulse amplitude, a pulse width, and a pulse frequency. In one example, each of the modulation functions is periodic to periodically modulate the at least one of the time-invariant pulse parameters. In one example, at least one of the modulation functions is non-periodic. In one example, the at least one non-periodic function arbitrarily modulates the at least one of the time-invariant pulse parameters. In one example, the at least one measurement for each of the applied time-varying pulse waveforms comprises an objective measurement obtained from the patient. In one example, the at least one objective measurement is obtained using the implantable stimulator device. In one example, the at least one objective measurement comprises at least one feature derived from of an electrospinogram (ESG) signal sensed at the implantable stimulator device. In one example, the at least one objective measurement comprises at least one feature derived from one or more evoked compound action potentials sensed at the implantable stimulator device. In one example, the evoked compound action potentials vary as the at least one of the time-invariant pulse parameters is modulated, and wherein the at least one objective measurement quantifies a degree of the variance of the evoked compound action potentials. In one example, the at least one objective measurement is obtained using a system separate from the implantable stimulator device. In one example, the at least one measurement for each of the applied time-varying pulse waveforms comprises a subjective measurement determined based on feedback from the patient. In one example, the at least one subjective measurement comprises a rating provided from the patient relevant to a symptom of the patient. In one example, the at least one subjective measurement comprises a stimulation threshold indicative of a strength of stimulation perceived by the patient. In one example, the at least one measurement for each of the applied time-varying pulse waveforms comprises at least one objective measurement obtained from the patient and at least one subjective measurement determined based on feedback from the patient. In one example, step (d) comprises determining a score for each of the applied time-varying pulse waveforms using the at least one measurement obtained for that time-varying pulse waveform, and selecting the one or more of the time-varying pulse waveforms for the patient using the determined scores. In one example, a plurality of measurements are obtained for each of the applied time-varying pulse waveforms, wherein each of the plurality of measurements are weighted when determining the score for each of the applied time-varying pulse waveforms. In one example, the method uses an external device in communication with the implantable stimulator device. In one example, step (a) is performed using the external device. In one example, the at least one measurement for each of the applied time-varying pulse waveforms is received at the external device, and wherein step (d) is performed using the external device. In one example, the method further comprises (e) using the external device to program the implantable stimulator device with the selected one or more of the time-varying pulse waveforms.

A method of adjusting stimulation for a patient having an implantable stimulator device is disclosed, which may comprise: (a) applying a waveform comprising time-varying pulses to the patient, wherein the time-varying pulses are formed using a modulation function to modulate at least one of a plurality of time-invariant pulse parameters of the pulses, wherein the modulation function comprises at least one of a modulation shape or modulation parameters that size the modulation shape; (b) obtaining at least one measurement for the applied waveform; (c) determining the effectiveness of the time-varying pulses for the patient using the at least one measurement; and (d) if the time-varying pulses are ineffective, adjusting the modulation function to adjust the time-varying pulses applied to the patient.

In one example, the method further comprises as an initial step determining the time-invariant pulse parameters for use with the patient. In one example, the at least one measurement obtained for the waveform is indicative of the effectiveness of the time-varying pulses for the patient. In one example, the method further comprises (e) repeating steps (a) through (d). In one example, the time-invariant pulse parameters comprise a pulse amplitude, a pulse width, and a pulse frequency. In one example, the modulation functions is periodic to periodically modulate the at least one time-invariant pulse parameter. In one example, the modulation function is non-periodic. In one example, the at least one non-periodic function arbitrarily modulates the at least one of the time-invariant pulse parameters. In one example, the at least one measurement for the applied waveform comprises an objective measurement obtained from the patient. In one example, the at least one objective measurement is obtained using the implantable stimulator device. In one example, the at least one objective measurement comprises at least one feature derived from of an electrospinogram (ESG) signal sensed at the implantable stimulator device. In one example, the at least one objective measurement comprises at least one feature derived from one or more evoked compound action potentials sensed at the implantable stimulator device. In one example, the evoked compound action potentials vary as the at least one of the time-invariant pulse parameters is modulated, and wherein the at least one objective measurement quantifies a degree of the variance of the evoked compound action potentials. In one example, the at least one objective measurement is obtained using a system separate from the implantable stimulator device. In one example, the at least one measurement for the applied waveform comprises a subjective measurement determined based on feedback from the patient. In one example, the at least one subjective measurement comprises a rating provided from the patient relevant to a symptom of the patient. In one example, the at least one subjective measurement comprises a stimulation threshold indicative of a strength of stimulation perceived by the patient. In one example, the at least one measurement for the applied waveform comprises at least one objective measurement obtained from the patient and at least one subjective measurement determined based on feedback from the patient. In one example, step (c) comprises determining a score for the applied waveform using the at least one measurement, and determining the effectiveness of the time-varying pulses for the patient using the score. In one example, the effectiveness of the time-varying pulses for the patient is determined by comparing the score to at least one threshold. In one example, a plurality of measurements are obtained for the applied waveform, wherein each of the plurality of measurements are weighted when determining the score for the applied time-varying pulses. In one example, the method uses an external device in communication with the implantable stimulator device. In one example, the at least one measurement for the applied waveform is received at the external device, and wherein steps (c) and (d) are performed using the external device. In one example, the modulation function is adjusted by adjusting the modulation shape. In one example, the modulation function is adjusted by adjusting one or more of the modulation parameters. In one example, the modulation function is adjusted by adjusting the at least one of the plurality of time-invariant pulses parameters that the modulation function modulates.

The invention may also reside in the form of a programed external device (via its control circuitry) for carrying out the above methods, a programmed IPG or ETS (via its control circuitry) for carrying out the above method, a system including a programmed external device and IPG or ETS for carrying out the above methods, or as a computer readable media for carrying out the above methods stored in an external device or IPG or ETS.

BRIEF DESCRIPTION OF THE DRAWINGS

FIG. 7A shows the modulation of one or more time-invariant tonic stimulation parameters as modulated by a modulation function to produce time-varying pulses (TVPs), while FIG. 7B shows an example of a Graphical User Interface (GUI) that can be used to prescribe and define the modulation function.

FIG. 10 shows an example of the manner in which the TVP algorithm can determine one or more best TVPs for a patient.

DETAILED DESCRIPTION

An increasingly interesting development in pulse generator systems, and in Spinal Cord Stimulator (SCS) pulse generator systems specifically, is the addition of sensing capability to complement the stimulation that such systems provide. Thus, IPGs such as IPG 100 as shown in FIG. 6A can include the ability to sense ElectroSpinoGram (ESG) signals in a patient's tissue.

Figure 6B:
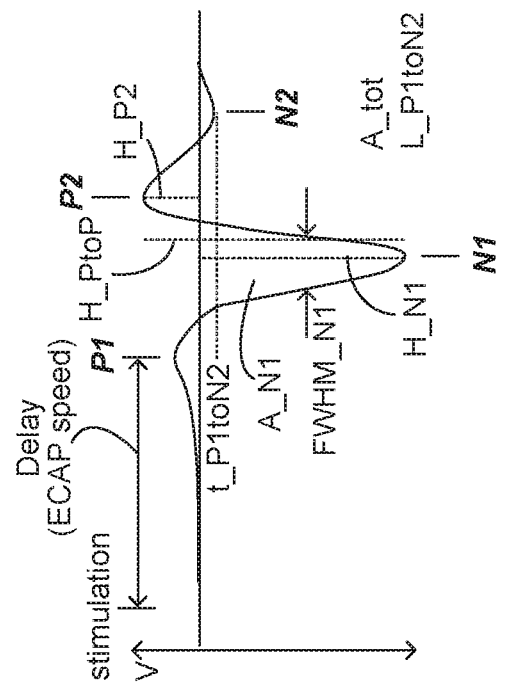
FIG. 6A and 6B show circuitry within an IPG or ETS for providing stimulation pulses, and for sensing an ElectroSpinoGram (ESG) signals in a patient's tissue.

For example, and as explained in U.S. Patent Application Publication 2017/0296823, it can be beneficial to sense in an ESG signal a neural response in neural tissue that has received stimulation from an SCS pulse generator. One such neural response is an Evoked Compound Action Potential (ECAP). An ECAP comprises a cumulative response provided by neural fibers that are recruited by the stimulation, and essentially comprises the sum of the action potentials of recruited neural elements (ganglia or fibers) when they "fire." An ECAP is shown in FIG. 6B, and comprises a number of peaks that are conventionally labeled with P for positive peaks and N for negative peaks, with P1 comprising a first positive peak, N1 a first negative peak, P2 a second positive peak and so on. Note that not all ECAPs will have the exact shape and number of peaks as illustrated in FIG. 6B, because an ECAP's shape is a function of the number and types of neural elements that are recruited and that are involved in its conduction. An ECAP is generally a small signal, and may have a peak-to-peak amplitude on the order of units to hundreds of microVolts depending on the amplification gain and location within the nervous system where these are sensed (brain, spinal cord, peripheral nervous system, somatic nervous system, motor elements, or other).

In another example, it can be useful to sense in an ESG signal a stimulation artifact, i.e., the voltage that is formed in the tissue as a result of the stimulation. Further details concerning the utility of sensing stimulation artifacts in an IPG system are disclosed in PCT Application Publication 2020/251899, which is incorporated by reference in its entirety. An ESG signal as can include other background signals that may be produced by neural tissue even absent stimulation, as explained the '899 Publication.

Figure 6A:
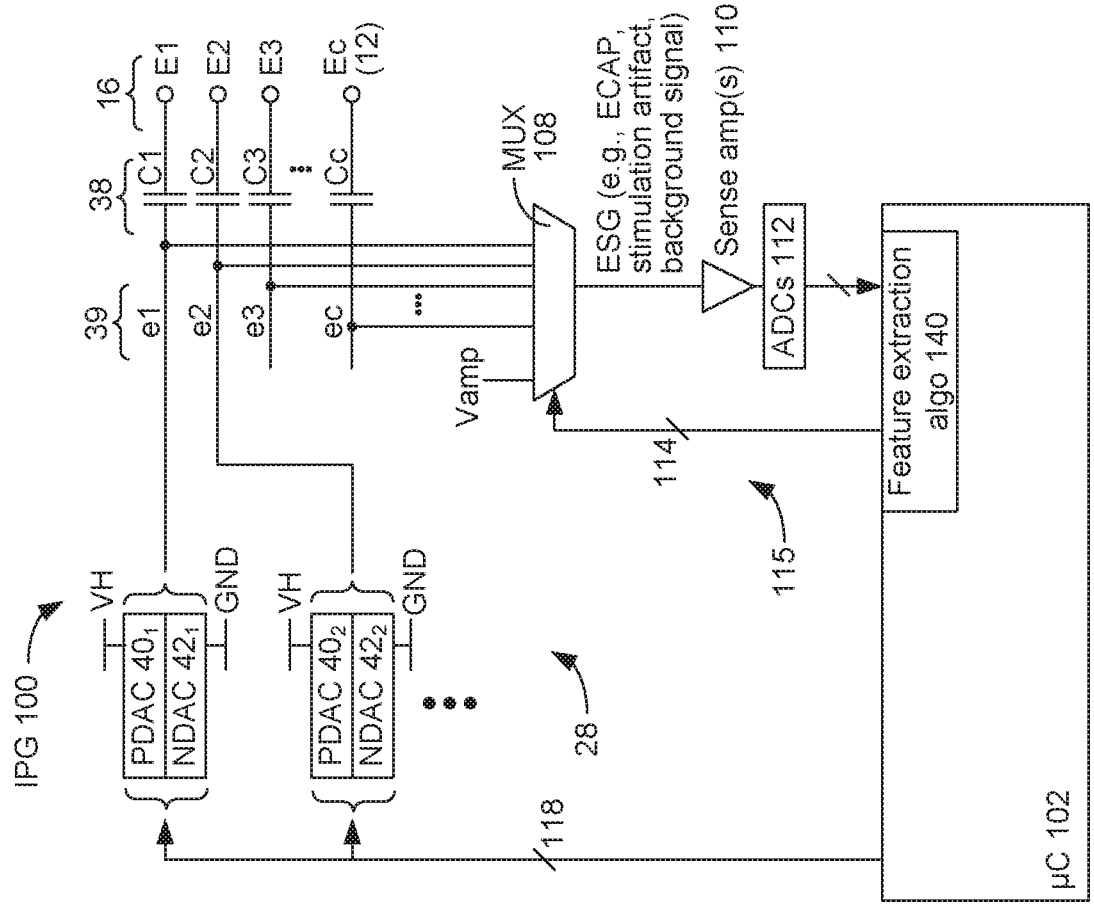

FIG. 6A shows circuitry for an IPG 100 that is capable of providing stimulation and sensing an ElectroSpinoGram (ESG) signal, which ESG signal may include ECAPs, stimulation artifacts, and other background signal as just mentioned. (This circuitry could also be present in an ETS as described earlier, although use in an IPG is discussed from this point forward for simplicity). Central to the IPG's circuitry is controller circuitry 102, which may comprise a microcontroller for example such as Part Number MSP430, manufactured by Texas Instruments, which is described in data sheets at http://www.ti.com/microcontrollers/msp430-ultra-low-power-mcus/overview.html, which is incorporated herein by reference. Other types of controller circuitry may be used in lieu of a microcontroller as well, such as microprocessors, FPGAs, DSPs, or combinations of these, etc. Controller circuitry 102 may also be formed in whole or in part in one or more Application Specific Integrated Circuits (ASICs), such as those described and incorporated earlier.

Figure 3:
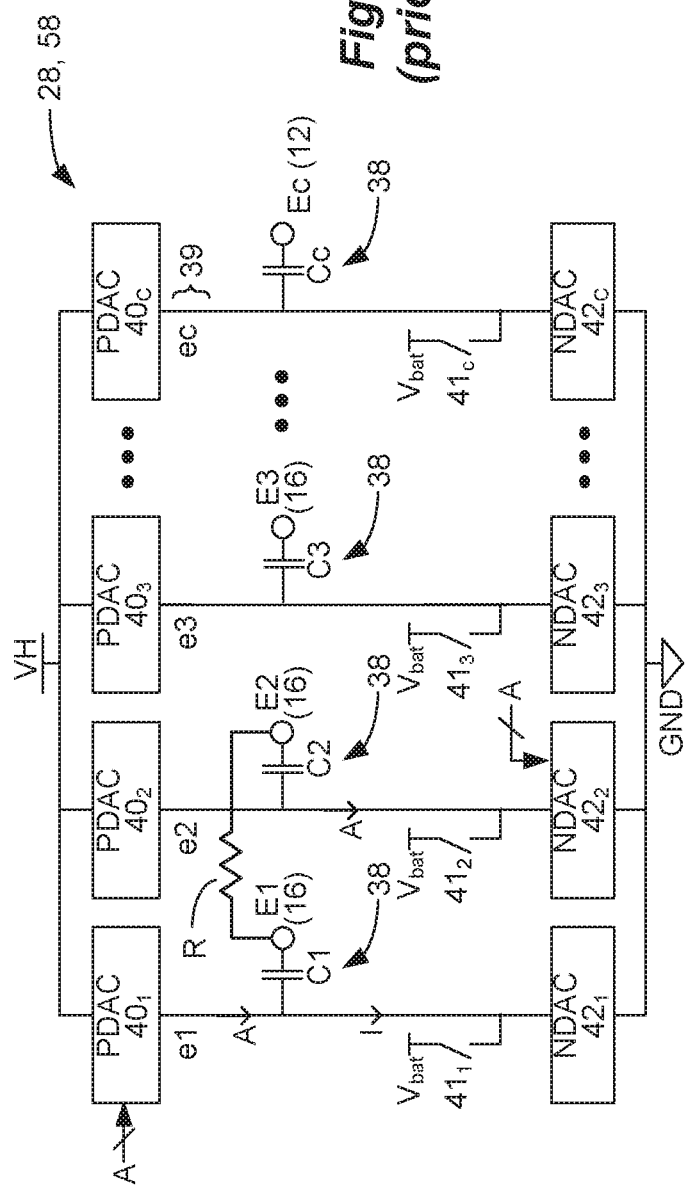
FIG. 3 shows stimulation circuitry useable in the IPG or ETS, in accordance with the prior art.

The IPG 100 also includes stimulation circuitry 28 to produce stimulation at the electrodes 16, which may comprise the stimulation circuitry 28 shown earlier (FIG. 3). A bus 118 provides digital control signals from the controller circuitry 102 (and possibly from an feature extraction algorithm 140, described below) to one or more PDACs $40_i$ or NDACs $42_i$ to produce currents or voltages of prescribed amplitudes (A) for the stimulation pulses, and with the correct timing (PW, F). As noted earlier, the DACs can be powered between a compliance voltage VH and ground. As also noted earlier, but not shown in FIG. 6A, switch matrices could intervene between the PDACs and the electrode nodes 39, and between the NDACs and the electrode nodes, to route their outputs to one or more of the electrodes, including the conductive case electrode 12 (Ec). Control signals for switch matrices, if present, may also be carried by bus 118. Notice that the current paths to the electrodes 16 include the DC-blocking capacitors 38 described earlier, which provide safety by preventing the inadvertent supply of DC current to an electrode and to a patient's tissue. Passive recovery switches $41_i$ (FIG. 3) could also be present, but are not shown in FIG. 6A for simplicity.

Figure 4:
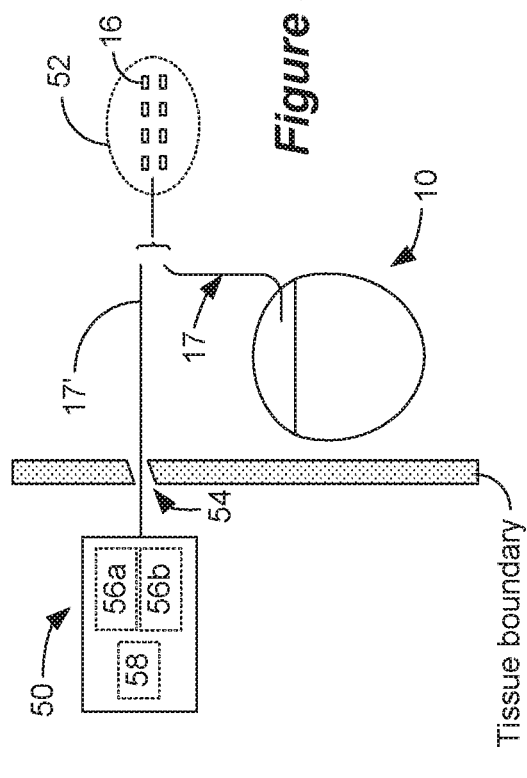
FIG. 4 shows an ETS environment useable to provide stimulation before implantation of an IPG, in accordance with the prior art.

IPG 100 also includes sensing circuitry 115, and one or more of the electrodes 16 can be used to sense signals the ESG signal. In this regard, each electrode node 39 is further coupleable to a sense amp circuit 110. Under control by bus 114, a multiplexer 108 can select one or more electrodes to operate as sensing electrodes by coupling the electrode(s) to the sense amps circuit 110 at a given time, as explained further below. Although only one multiplexer 108 and sense amp circuit 110 is shown in FIG. 4A, there could be more than one. For example, there can be four multiplexer 108/sense amp circuit 110 pairs each operable within one of four timing channels supported by the IPG 100 to provide stimulation. The sensed signal are preferably converted to digital signals by one or more Analog-to-Digital converters (ADC(s)) 112, which may sample the waveform at 50 kHz for example. The ADC(s) 112 may also reside within the controller circuitry 102, particularly if the controller circuitry 102 has A/D inputs. Multiplexer 108 can also provide a fixed reference voltage, Vamp, to the sense amp circuit 110, as is useful in a single-ended sensing mode.

So as not to bypass the safety provided by the DC-blocking capacitors 38, the input to the sense amp circuitry 110 is preferably taken from the electrode nodes 39, and so the DC-blocking capacitors 38 intervene between the electrodes 16 where the signals are sensed and the electrode nodes 39. However, the DC-blocking capacitors 38 will pass AC signal components while blocking DC components, and thus AC signals will still readily be sensed by the sense amp circuit 110. In other examples, signals may be sensed directly at the electrodes 16 without passage through intervening capacitors 38.

As shown, a feature extraction algorithm 140 is programmed into the controller circuitry 102 to receive and analyze the digitized ESG signals. One skilled in the art will understand that the feature extraction algorithm 140 can comprise instructions that can be stored on non-transitory machine-readable media, such as magnetic, optical, or solid-state memories within the IPG 100 (e.g., stored in association with controller circuitry 102).

The feature extraction algorithm 140 operates within the IPG 100 to determine one or more features, generally speaking by analyzing the size and shape of the sensed signals. For an ECAP as described earlier, the feature extraction algorithm 140 can determine one or more ECAP features (EFx), which may include but are not limited to:

- a height of any peak (e.g., H_N1) present in the ECAP;
- a peak-to-peak height between any two peaks (such as H_PtoP from N1 to P2);
- a ratio of peak heights (e.g., H_N1/H_P2);
- a peak width of any peak (e.g., the full width half maximum of a N1, FWHM_N1);
- an area under any peak (e.g., A_N1);
- a total area (A_tot) comprising the area under positive peaks with the area under negative peaks subtracted or added, also known as area under the curve;
- a length of any portion of the curve of the ECAP (e.g., the length of the curve from P1 to N2, L_P1toN2)
- any time defining the duration of at least a portion of the ECAP (e.g., the time from P1 to N2, t_P1toN2);
- a time delay from stimulation to issuance of the ECAP, which is indicative of the neural conduction speed of the ECAP, which can be different in different types of neural tissues;
- a rate of variation of any of the previous features, e.g., a difference between the previous value of the feature and the new value of the feature in the new stimulation period;
- any mathematical combination or function of these variables (e.g., H_N1/FWHM_N1 would generally specify a quality factor of peak N1);
- any simplified version of the previous features that acts as a proxy for the specified feature. For example, instead of area under the curve, the sum of the absolute value of the sensed samples over the specified time interval; or instead of computing the length of the curve using Euclidean distance in a time interval, the length of the curve is computed as the sum of the absolute value of the difference of consecutive sensed samples; or instead of the height of N1 to P2 (H_PtoP), the maximum minus the minimum in a specified time interval, also known in statistics as the range of the sensed samples in a specified time interval. Such simplified features can be extracted directly using the hardware in the IPG;
- any of the previous features computed over any time interval t1 and t2, where t1 is the start of the time interval and t2 is the end of the time interval, and where t1 and t1 can be referred to the beginning of the stimulation pulse.

The feature extraction algorithm 140 can also determine one or more stimulation artifact features (SAFx), as explained in the above-incorporated '899 Publication.

Once the feature extraction algorithm 140 determines one or more of these features, it may then adjust the stimulation that the IPG 100 provides, for example by providing new data to the stimulation circuitry 28 via bus 118. This is explained further in U.S. Patent Application Publications 2017/0296823 and 2019/0099602, which uses ECAP features to adjust stimulation. In one simple example, the feature extraction algorithm 140 can review the height of the ECAP (e.g., its peak-to-peak voltage) or the height of the ESG signal in any predefined time interval such as 0.6 ms to 2.2 ms, and in closed loop fashion adjust the amplitude I of the stimulation current to try and maintain the height in the interval or the height of the ECAP to a desired value. The above-incorporated '899 Publication discloses that features of stimulation artifacts within the ESG signal can also be used to control stimulation.

Figure 2B:
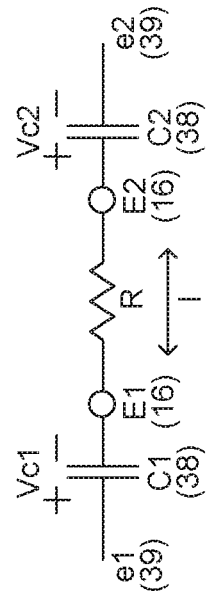
FIGS. 2A and 2B show an example of stimulation waveforms producible by the IPG or in an External Trial Stimulator (ETS), in accordance with the prior art.
Figure 2A:
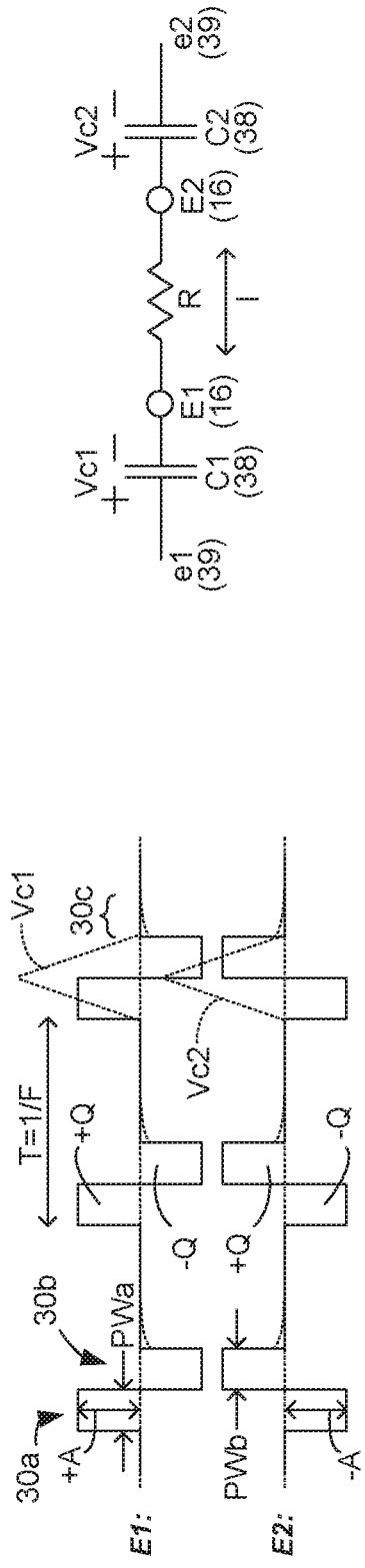

Conventional neuromodulation therapies employ electrical stimulation pulse trains at low- to mid-frequencies (e.g., F<1500 Hz) to efficiently induce desired firing rate of action potentials from electrical pulses (e.g., one pulse can induce a burst of action potentials, or multiple pulses may be temporally integrated to induce one action potential). Such stimulation pulse trains are usually tonic, i.e., the amplitude (A), pulse width (PW), and frequency (F) are fixed, as shown in FIG. 2A for example. However, it is known that neural tissue may accommodate, adapt, and/or habituate to a continuous tonic input, resulting in a diminished neural response over time.

Recently, high frequency stimulation (e.g., F=1.5 kHz to 50 kHz) has been employed to block naturally occurring action potentials within neural fibers or otherwise disrupt the action potentials within the neural fibers, as can be useful in pain management. Although the underlying mechanisms are unclear as to why high frequency stimulation can provide effective pain reduction, it has been hypothesized that depletion of neurotransmitters, desynchronized firing of multiple neurons, and generation of stochastic noise may be factors that explain such success. Nevertheless, high frequency stimulation is disadvantageous because it consumes excessive energy, thereby requiring the IPG 100 to have a larger battery 14 (if the battery is permanent), or to be charged more often (if rechargeable).

In response to such concerns, the art has taught (see, e.g., U.S. Patent Application Publication 2017/0266447, which is incorporated herein by reference in its entirety) that it can be useful to modulate otherwise time-invariant tonic stimulation pulses (with a fixed amplitude, pulse width, and frequency) to provide stimulation to an SCS patient. Specifically, the art teaches that a modulation function 150 can be applied to one or more of the stimulation parameters used during tonic stimulation to create a waveform where the pulses vary, as shown in a few examples (150a-150c) in FIG. 7A. Providing such a modulation function 150 varies the stimulation pulses provided to the patient over time, and therefore, may mitigate or prevent the loss of therapeutic response possibly caused by accommodation, adaptation, and/or habituation of neural tissue to the stimulation. Moreover, use of a modulation function 150 is hypothesized to provide significant pain management to patients, even at lower frequencies, thus providing solutions that are more considerate of energy consumption and that are not as taxing on the IPG's battery 14.

A modulation function 150 comprises a modulation shape and one or more modulation parameters that size the modulation shape, and is applied to one or more tonic stimulation parameters. Note in FIG. 7A that tonic stimulation parameters (e.g., amplitude, pulse width, frequency) suitable for a particular patient may already be known and may have been determined during a fitting process. Such a fitting process can involve, using a clinician programmer 70 (FIG. 5) or other external device, trying various simulation parameters on an implanted patient (e.g., having an IPG 100) to determine what parameters work best for the patient. Assessing the success of various stimulation parameters can involve the use of subjective measurements, such as by receiving feedback from the patient as to how the stimulation parameters are affecting his symptoms. Assessing the success of various stimulation parameters can also involve the use of objective measurements taken form the patient, such as by assessing one or more ECAP features or other objective measurables, as described for example in U.S. Patent Application Publication 2020/0230410, which is incorporated herein by reference in its entirety. Note that proper fitting of stimulation to a patient can also involve determining a proper electrode configuration—i.e., which electrodes in the electrode array should be active, and the amplitude and polarity of those electrodes. Although not shown, a tonic stimulation parameter can also comprise an on-off duty cycle, which specifies repeating on duration for simulation (e.g., 100 ms, or some number of pulses), and an off duration (e.g., 1 s).

Figure 7A:
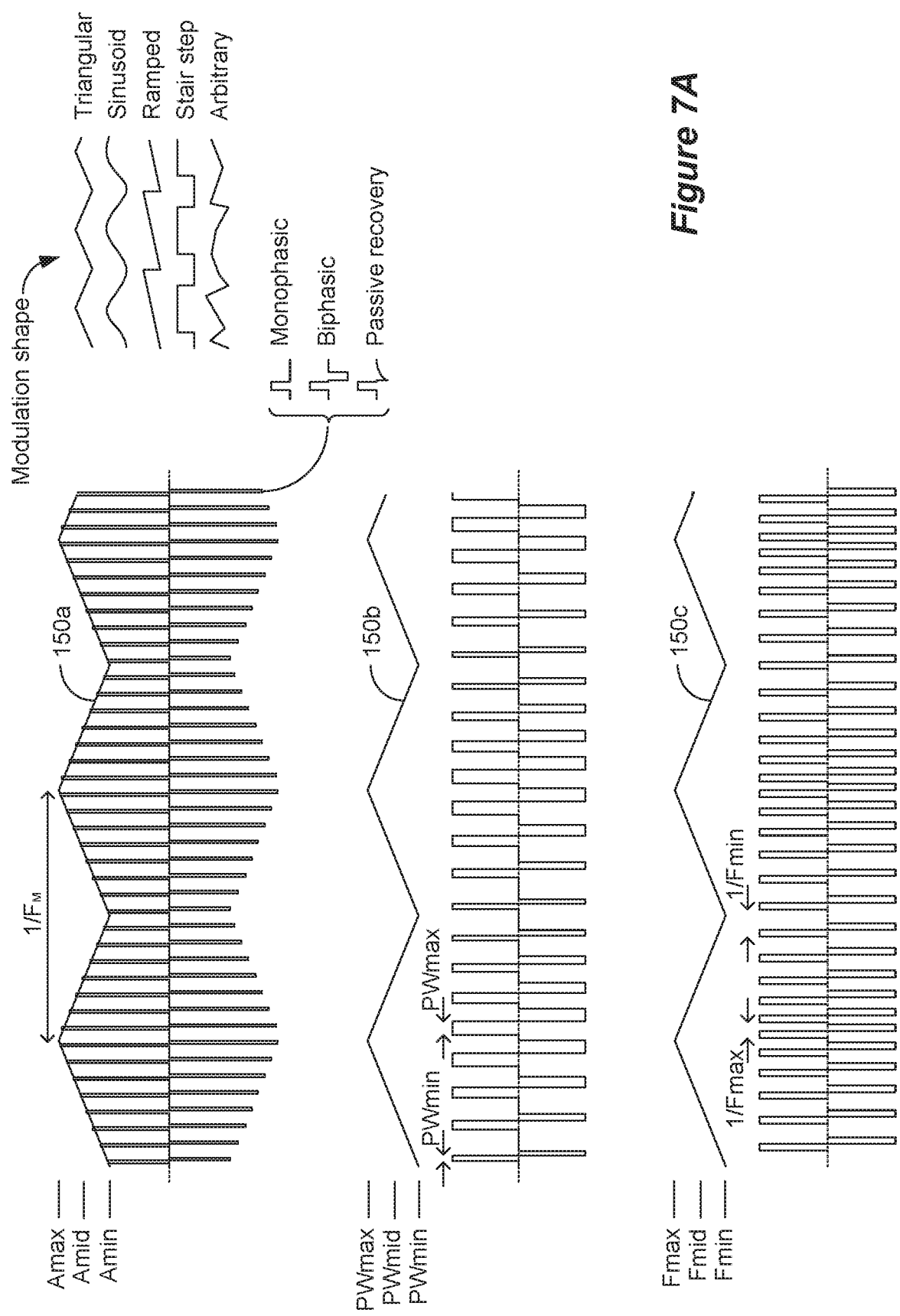

Assume in the examples of FIG. 7A that the tonic situation pulses (unvaried by a modulation function 150) have an amplitude A of 4 mA, a pulse width PW of 500 µs, and a frequency F of 200 Hz. Modulation function 150a in FIG. 7A applies an amplitude modulation to the tonic stimulation pulses, and so modulates the otherwise invariant amplitude (4 mA) of the tonic pulses. In this example, the shape of modulation function 150a is triangular, and thus gradually ramps the amplitude of the pulses up and down. However, this is just one example of a modulation shape, and different shapes could be used as well. For example, the right of FIG. 7A shows sinusoid, ramped, stair step, and even arbitrary modulation shapes. Although not shown, modulation shapes could also comprise various statistical distribution functions, such as Poisson, Uniform, Gibbs, Gaussian, Borel, or Boltzman distributions, etc.

The modulation function 150a (FIG. 7A), is applied to the tonic amplitude to define a series of consecutive pulses with time-varying amplitude as shown. The modulation function is defined and sized by various modulation parameters, such as Amax and Amin, which specify a maximum and minimum amplitude for the pulses. Amax for example may equal the prescribed tonic amplitude (4 mA), while Amin would be less (e.g., 2.5 mA). Amax and Amin can also comprise scalars to be applied to (e.g., multiplied with) the tonic amplitude. For example, Amax may equal 1 to produce the highest-amplitude pulses (e.g., 4 mA*1=4 mA), while Amin may equal 0.625 to produce the lowest-amplitude pulses (e.g., 4 mA*0.625=2.5 mA). Another modulation parameter, Amid, may be defined as a value (or scalar) between the maximum and minimum values. For example, if Amid is midway between Amax and Amin, it would comprise a value of 3.25 mA, or a scalar of 0.8125. Amid can be defined in accordance with the modulation function, and may for example comprise a value such that the area of the modulating function over Amid equals the area of the modulating function under Amid. In this respect, Amid may not necessarily be midway between Amin and Amax if the shape of the modulation function 150 is non-symmetrical. Amid can also be defined as the mean or the median of the distribution of amplitude values generated by the modulation function as the time is varied, independently on whether the modulation function is periodic or non-periodic.

Although not strictly necessary, the modulation shape of the modulation function may be periodic (repeating) in nature, and may have a modulation frequency, $F_M$, another modulation parameter that specifies how quickly the modulation changes. As an example, in the case of amplitude modulation, $F_M$ is the frequency at which pulses of a given amplitude will repeat, as shown in FIG. 7A. $F_M$ is preferably lower than the frequency F of the individual tonic pulses, and could for example vary between 0.1 and 20 Hz, or even at lower or higher frequencies as technology evolves and enables faster sampling frequencies with low energy consumption. Similarly, in the case of pulse width modulation or frequency modulation, $F_M$ is the frequency at which pulses of a given pulse width or frequency repeat, again as shown in FIG. 7A The modulation function 150a can be applied to modulate the amplitude of tonic pulses of all kinds. In the various waveforms shown in FIG. 7A, the pulses are biphasic, and more specifically symmetrically biphasic, having pulse phases of opposite polarities but with the same amplitude and pulse width. Non-symmetric biphasic pulses could also be used. Additionally, the pulses may be monophasic, and could involve the use of passive charge recovery, as discussed earlier.

Modulation function 150b, also of triangular shape, varies a different tonic stimulation parameter, specifically the pulse width of the tonic pulses. Modulation function 150b is applied to the tonic pulse width to define pulses with pulse widths that vary over time as shown. The modulation function 150b is defined and sized by various modulation parameters and again specifies maximum (PWmax), minimum (PWmin), and midpoint (PWmid) pulse width values. For example, if the tonic pulses nominally have a pulse width of 500 µs, PWmim and PWmax could be set to 300 µs and 600 µs respectively (i.e., scalars of 0.6 to 1.2), with PWmid comprising 450 µs (a scalar of 0.9). As before, modulation function 150b can have different shapes and be applied to different kinds of pulses, and may be periodic having a modulation frequency $F_M$. Modulation function 150c is similar, but varies the tonic stimulation parameter of frequency. For example, if the tonic pulses nominally have a frequency of 200 Hz, Fmin and Fmax could be set to 100 Hz and 300 Hz respectively (i.e., scalars of 0.5 and 1.5), with Fmid comprising 200 Hz (a scalar of 1.0). Although not shown, a modulation function can also be applied to other tonic stimulation parameters, such as the on-off duty cycle described earlier.

Although not illustrated in FIG. 7A, note that more than one stimulation parameter can be modulated at any given time. For example, the amplitude (150a) can be modulated while the pulse width (150b) and/or frequency (150c) is also modulated. Such modulation may occur on different time scales, i.e., $F_E$ for each could be different.

FIG. 7B shows a Graphical User Interface (GUI) 160 that may be rendered on an external device, such as the external controller 60 or the clinician programmer 70 (FIG. 5), that can be used to control the stimulation the IPG 100 provides. In this GUI 160, a user can define a modulation function 150 to be applied to tonic stimulation pulses. It is assumed here that the tonic stimulation pulses (e.g., A, PW, f) have been defined for the patient elsewhere in the GUI 160 (during a fitting procedure), although definition of the tonic stimulation pulses could also occur using the same screen shown in FIG. 7B. In GUI 160, a user can choose one or more modulation shapes (162), and one or more a tonic stimulation parameters to which that shape (modulation function) will be applied (163). The user can also select one or more modulation parameters (164) to size the modulation function 150 of the desired shape.

Assuming that the user wishes to define a modulation function 150a that modulates amplitude as set described in FIG. 7A, the user in FIG. 7B can select a triangular shape, and relevant amplitude modulation parameters. For example, the user can enter maximum and minimum amplitudes 4.0 and 2.5 mA (or scalars such as 1 and 0.625 as described above). The software in the external device (e.g., 84, FIG. 5) can then determine (using the selected modulation shape) a midpoint of 3.25 mA (or a scalar of 0.8125) and a percentage that the modulation function will spread around this midpoint (e.g., 23%. Note that 3.25+0.23(3.25)=4 mA, and 3.25−0.23(3.25)=2.5 mA). Alternatively, the user can define the midpoint and the spread, with the software working backwards to calculate the maximum and minimum values. The user can also select the modulation frequency FM (e.g., 0.5 Hz). Once a modulation function 150 has been defined, the software (e.g., 84, FIG. 5) can automatically compile the proper programming instructions to allow the IPG 100 to form the tonic stimulation pulses as modulated by the modulation function 150. Alternatively, the modulation function 150 can be provided to the IPG 100 along with the tonic stimulation parameters, leaving it to the IPG 100's controller circuitry 102 (FIG. 6A) to then form the time-varying modulated pulses.

While the creation of time-varying pulse waveforms has to this point been described as involving the application of a modulation function 150 to one or more tonic stimulation parameters, this is not strictly necessary. Instead, time-varying pulses could be specified in any manner, and again can comprise pulses that vary randomly, or even arbitrarily. In this regard, time-varying pulses need not be defined with respect to tonic stimulation parameters modulated by a modulation function 150.

Figure 5:
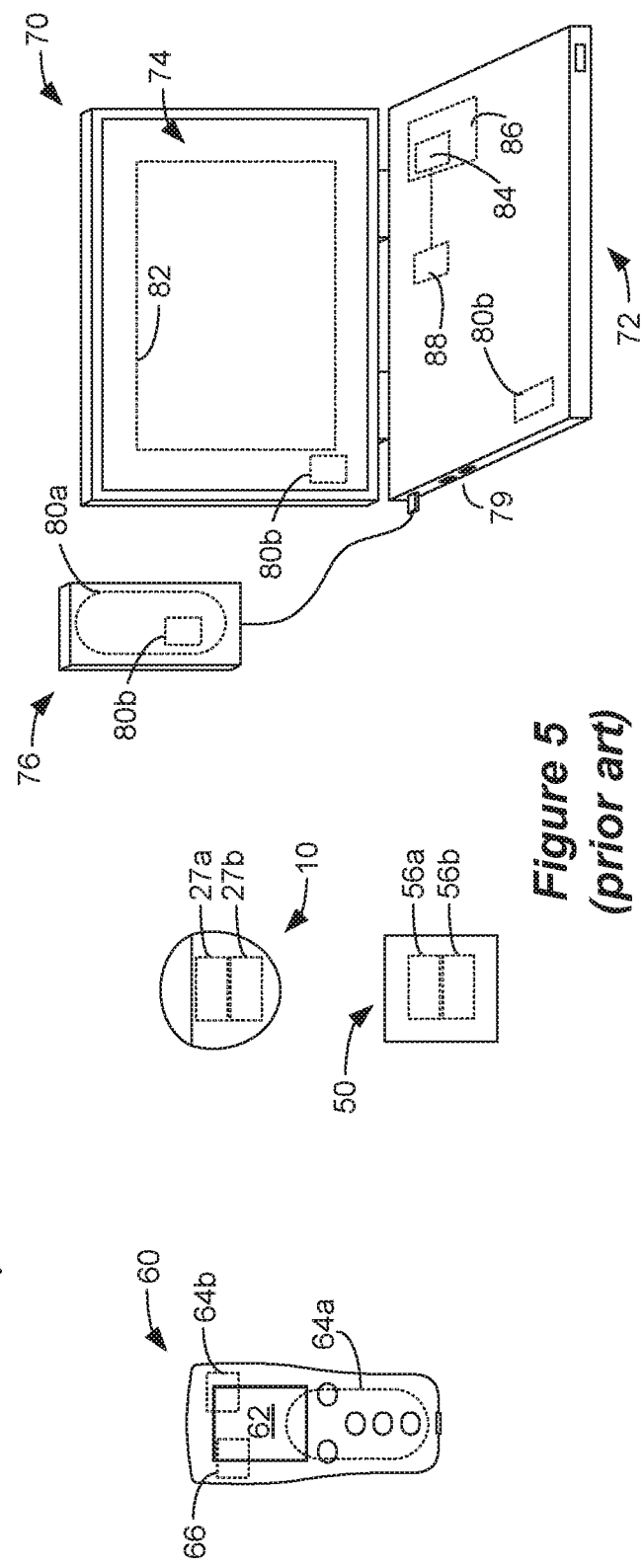
FIG. 5 shows various external devices capable of communicating with and programming stimulation in an IPG and ETS, in accordance with the prior art.
Figure 8:
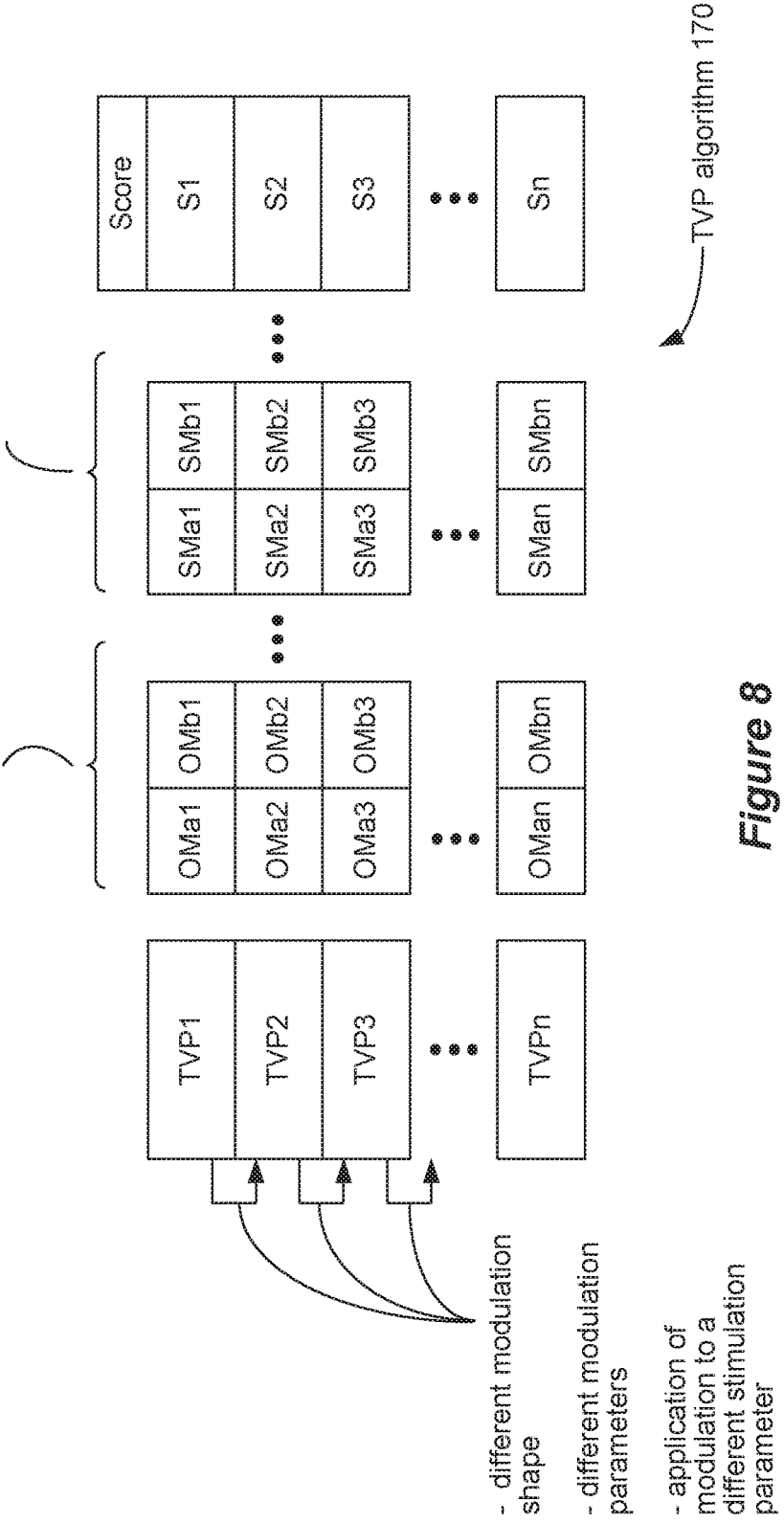
FIG. 8 shows an example of a time-varying pulse (TVP) algorithm useful to determine one or more best TVPs for a patient, where the algorithm uses one or more objective or subjective measurements to determine a TVP score for the patient.

FIG. 8 shows an algorithm 170 used to assess and determine one or more best time-varying pulses (TVPs) for a given patient. N candidate TVPs (TVP1-TVPn) are shown, and will be tested on a given patient having IPG 100 (or an ETS). The TVPs can be defined using the GUI 160 described earlier (FIGS. 7A and 7B), or otherwise. One or more measurements are taken during the application of a given TVP to the patient, and such measurements may be objective or subjective in nature. A number of objective measurements which can be taken for each TVP are shown in FIG. 8 (OMa, OMb, etc.), as are a number of different subjective measurements (SMa, SMb, etc.). The algorithm 170 may use one or more objective measurements, and one or more subjective measurements. Alternatively, the algorithm 170 may only use one or more objective measurements, or only use one or more subjective measurements. Ultimately, the algorithm 170 computes a score (Sx) for each TVP using the one or more objective and/or subjective measurements, which are used to determine a best one or more TVPs to use for the patient as therapy going forward, as explained further below. In one example, algorithm 170 may be executed during a patient's fitting process, and thus may be implemented in the clinician programmer 70's software 84 (FIG. 5). Preferably, algorithm 170 is executed after determination of tonic stimulation parameters (e.g., amplitude, pulse width, frequency) that are appropriate for the patient.

Preferably each of the TVPs to be tested during TVP algorithm 170 are different and result in the application of different time-varying pulse waveforms to the patient. The TVPs may be made different by varying the modulation function 150 applied to tonic stimulation parameters. For example, the shape of the modulation function 150 can be changed, with TVP1 using a triangular shaped modulation function 150, TVP2 using a sinusoidal shaped function, etc.

Further, the TVPs may be made different by changing the modulation parameters used to size the modulation shape. For example, TVP1 may set particular values (or scalars) for Amax and Amin. TVP2 may change Amin to a different value, while TVP3 may change Amax to a different value, which would also work to change Amid and spread. Modulation frequency FM may also be changed between the various TVPs. Still further, the TVPs may be made different by applying a modulation function 150 to a different one of the tonic stimulation parameters (e.g., A, PW, or F). For example, TVP1 may involve use of a first modulation function that varies amplitude (150a, FIG. 7A), TVP2 may involve the use of a second modulation function that varies pulse width (150b, FIG. 7A), and TVP3 may involve use of a third modulation function that varies frequency. To stress a point made earlier, TVPs can be defined without the application of a modulation function 150 to otherwise tonic stimulation, and in this regard the TVPs can be made different in other manners that do not necessarily involve changing a modulation function per se. The TVPs to be tried during execution of the TVP algorithm 170 may be determined based on clinical experience as those understood based on previous use as being most relevant to affecting patients' symptoms.

Figure 1:
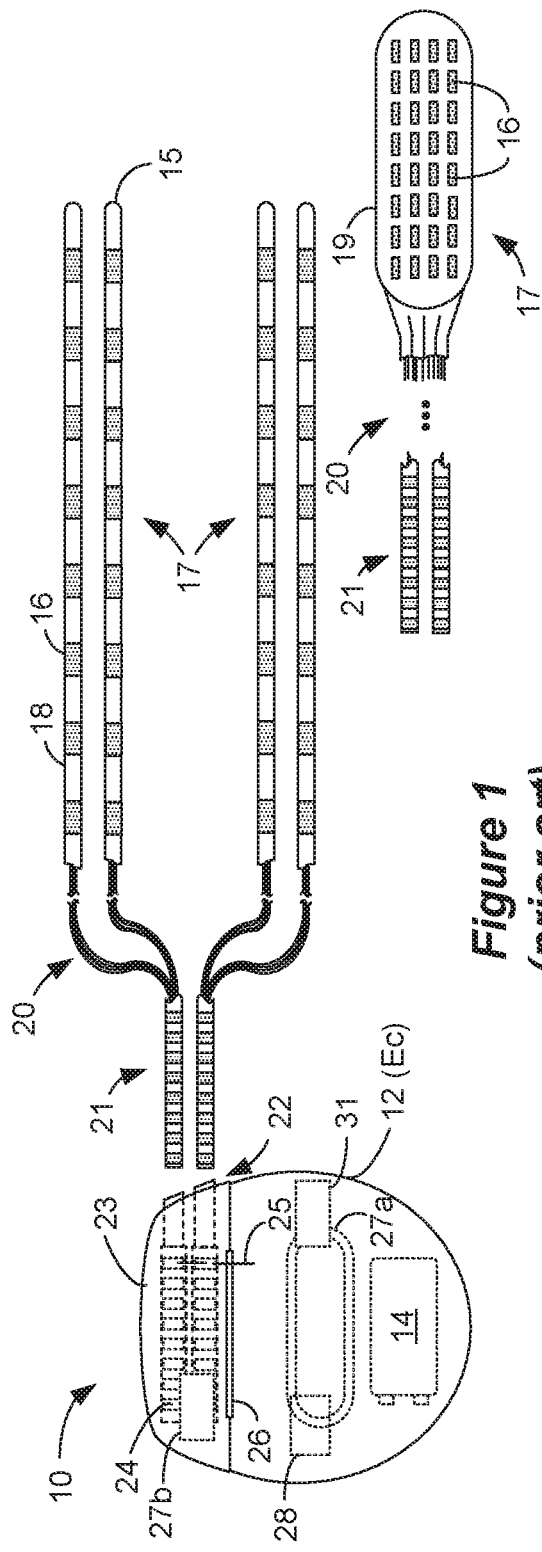
FIG. 1 shows an Implantable Pulse Generator (IPG), in accordance with the prior art.

As mentioned, during the application of each TVP to the patient, one or more objective measurements can be made. Such measurements can include for example one or more features of an ESG signal sensed by the patient's IPG 100 or ETS. Such ESG features can include ECAP features (as explained with particularity further below with reference to FIG. 9), ECAP threshold, stimulation artifact features, or background signal features. An ECAP threshold is defined as the minimum amplitude required for the IPG to detect the ECAP response. Still other objective measurables can be used by TVP algorithm 170 that are indicative of a patient's symptoms, such as pain in an SCS application. Such objective measurements may not comprise measurements that are made using the patient's IPG or ETS. For example, EEG, heart rate, blood pressure, and respiration rate may all comprise objective measurements that can be used by TVP algorithm 170. Such measurements may be taken by medical equipment apart from the patient's IPG or ETS, and may be provided to the external device (e.g., clinician programmer 70) that executes the TVP algorithm 170. For example, if blood pressure is used as an objective measurement, a patient's blood pressure readings can be transmitted (either by wire or wirelessly) to the clinician programmer 70. Measures of a patient's posture can also comprise an objective measure, as posture can affect a patient's symptoms and the therapy that would best be applied to the patient. In this regard, the accelerometer 31 in the IPG (FIG. 1) can also be queried.

One or more subjective measurements can also be made during the application of each TVP to the patient, which such subjective measures being dependent on patient feedback and hence subjective in nature. Such subjective measurements can be input by the clinician into the clinician programmer 70 so that they can be received by the TVP algorithm 170. Subjective measurements can also be entered by the patient using the clinician programmer 70 or his patient external controller 60.

As an example of a subjective measurement, for a given TVP, the patient can provide a pain score indicating how well the TVP is affecting the patient's symptoms (e.g., with 1 indicating great pain relief and 10 indicating poor pain relief). The patient may also rank the quality of sensation, or provide an indication as to how well the TVP appears to be addressing or covering the patient's symptoms. In short, subjective measurement can comprise various ratings provided from the patient relevant to a symptom of the patient. Other subjective measures that can also be rated by the patient and used with TVP algorithm 170 include: pain duration, frequency of pain episodes, duration of pain episodes, intensity of pain episodes, estimated body volume of pain areas during pain episodes, duration of patient-specific activities (previously reduced or affected by the pain), mobility as a trigger for pain episodes, satisfaction ratings, etc.

Additionally, subjective measurements can include various thresholds, such as a paresthesia threshold (Pth) at which stimulation can be felt by a patient (paresthesia), or a discomfort threshold (Dth) where the stimulation is too intense. For example, during each TVP, the amplitude of the stimulation can be adjusted, with the paresthesia threshold comprising a lowest amplitude (or other measure of energy) at which a patient can feel the stimulation. The discomfort threshold can comprise a highest amplitude (or other measure of energy) that the patient can tolerate. In short, Pth and Dth comprise stimulation thresholds indicative of a strength of stimulation perceived by the patient that are used to guide the selection of the modulation parameters for a TVP. Note that TVPs can also be used for SCS sub-perception therapy, meaning that stimulation that is not perceived by the patient but is still continuously varying in time.

Figure 9:
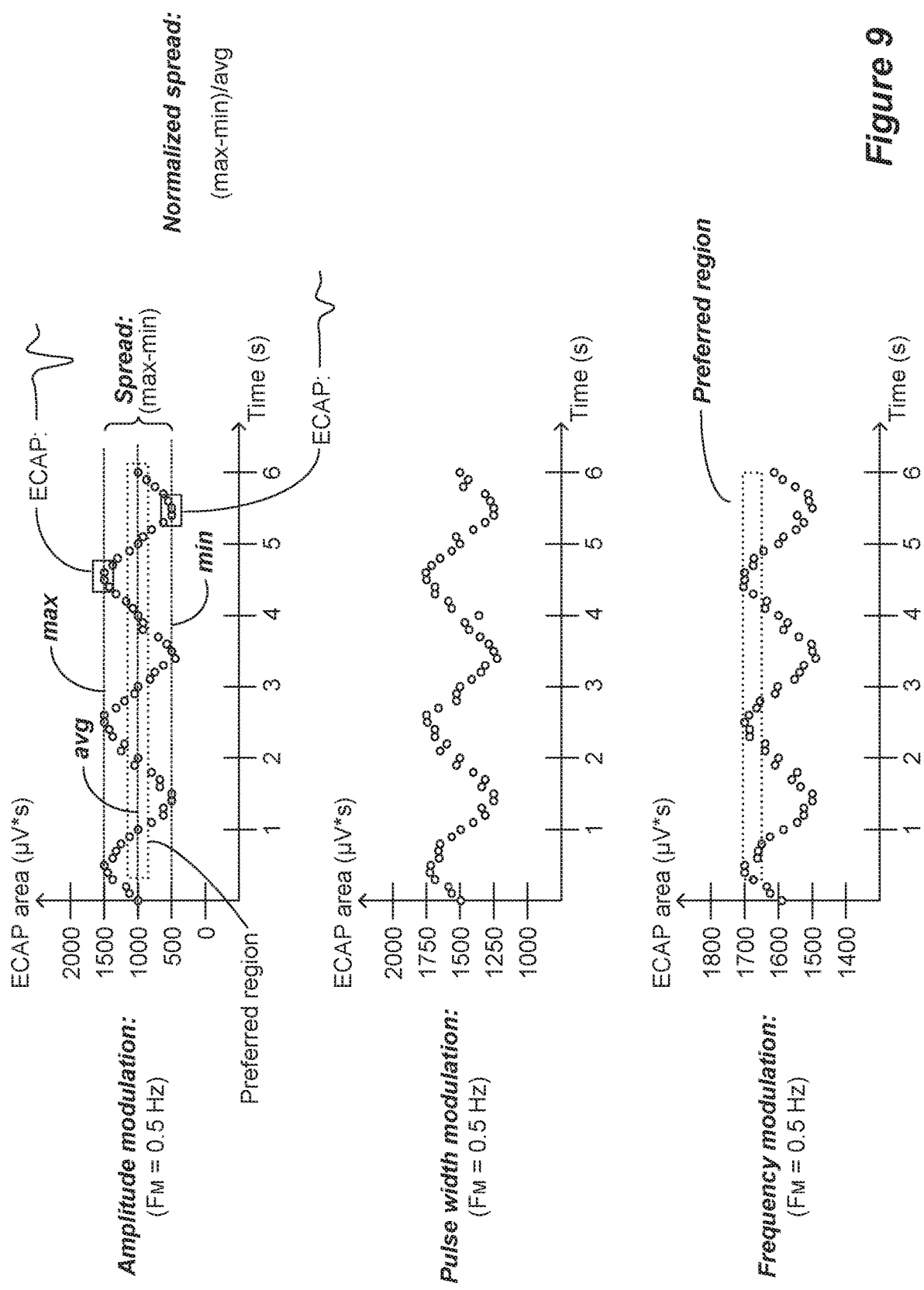
FIG. 9 shows examples of objective measurements that can be used in the TVP algorithm.

FIG. 9 describes further details of objective measurements that can be used by TVP algorithm 170 that are gleaned from ECAPs measurable by the patient's IPG or ETS, and shows the effect of time-varying modulation on such measurements. In this example, a particular ECAP feature—namely the area under the curve of the ECAP ($\mu V*s$) ("ECAP area")—is measured as a function of time. In FIG. 9, to ease illustration, several area values from several stimulation pulses are averaged. A sinusoid modulation function shape (see FIG. 7A) is applied to tonic stimulation pulses with a modulation frequency FM of 0.5 Hz, with the sinusoid modulation function applied to modulate amplitude (top), pulse width (middle) and frequency (bottom). As can be seen, the ECAP area (which relates generally to the size of the ECAP) varies with a periodicity matching that of the modulation function. During periods where modulation results in pulses with higher pulse amplitudes, longer pulse widths, or higher frequencies, the ECAP area is larger; during periods where modulation results in pulses with lower pulse amplitudes, shorter pulse widths, or lower frequencies, the ECAP area is smaller. Although FIG. 9 illustrates ECAP area as the relevant feature, it would be expected that other ECAP features such as those mentioned above would be similarly affected by the applied modulation.

The data in FIG. 9 illustrates many potential objective measurements that can be used in the TVP algorithm 170, such as maximum, minimum, and average ECAP area. Again, other features beyond ECAP area could be used as well. Still other objective measurements can be determined that are indicative of how strongly the modulation is affecting the feature. The difference between the maximum and minimum areas—the spread between the two—provides one such measurement. The spread of this feature (or other features) may be normalized using the average, i.e., (max−min)/avg. This can be useful because different modulation schemes may affect the ECAP feature differently. For example, when amplitude modulation is used in FIG. 9, the average is relatively low (1000), but the spread (1500-500) is high, leading to a normalized spread of 1. When pulse width modulation is used, the average is higher (1500), but the spread is lower (1750-1250), leading to a normalized spread of 0.33. When frequency modulation is used, the average is still higher (1600), and the spread is still lower (1700-1500), leading to a normalized spread of 0.125. These normalized spreads indicate in this example that amplitude modulation produces the largest effect on resulting ECAPs, which may or may not be desirable for the patient depending on the circumstances. Pulse width modulation produces a smaller effect on the resulting ECAPs, with frequency modulation producing a still smaller effect. This may of course be due to the particular modulation parameters used for the three different types of modulation illustrated in FIG. 9. In short, an objective measurement can comprise any metric that quantifies a degree of the variance in the measured response, such as the variance in an ECAP feature.

FIG. 9 also illustrates that there may be preferred values for the given measurable which lead to the best clinician outcomes. For example, it may be known when amplitude modulation is used that the best clinical outcomes are observed when the ECAP area varies within a particular range, such as from 800 to 1200. It may also be known when frequency modulation is used that the best clinical outcomes are observed when the ECAP area varies within a range (e.g., from 1650 to 1700), as shown in FIG. 9. In this regard, another objective measurable which can be gleaned from FIG. 9 and used in TVP algorithm 170 is the extent to which a particular modulation scheme results in ECAP areas (or other features) within such preferred regions. The TVP algorithm 170 may compute or determine a fit metric (another objective measurement) that quantifies how well the resulting ECAP area matches such preferred regions or other desired ECAP area thresholds, or fit metrics for any other feature extracted from the ECAP response within the ESG.

Once relevant objective and/or subjective measurements have been determined for each TVP tested, the TVP algorithm 170 may compute a score for each, and FIG. 10 shows a simple example. In this example, one objective measurement is used by the algorithm, specifically the normalized spread of ECAP area which was explained earlier with reference to FIG. 9. Further, two subjective measurements are used, specifically a pain score, and a perception threshold Pth. Again many other objective and/or subjective measurements can be used, such as those described earlier, and use of these three measurements provides only a simple example.

In this example, the algorithm 170 computes a score for the TVP as a function of the measurements, and this can occur in several different manners. In FIG. 10, the three measurements are weighted by multiplying each by a weight w1, w2, and w3. The values of the weights used in the TVP algorithm 170 can be set empirically to emphasize the importance of each measurements in the overall score calculation. In the example of FIG. 10, w1=1, w2=−0.05, and w3=−0.1, which generally tends to normalize each of the measurements to approximately the same magnitude. Weights w2 and w3 are negative because they are applied to measurements that denote worse results at higher numbers (i.e., it would be preferred that pain scores and Pth are low). In the score calculation example of FIG. 10, the weighted measurements are then added. It is assumed in this example that higher score values indicate better results, although lower scores could also indicate better performance depending on the way in which the score is calculated. If a single measurement is used by TVP algorithm 170, note that the score for each TVP could be determined by, or comprise, that single measurement.

TVP2 has been shown by TVP algorithm 170 to comprise the most effective treatment for the patient (−0.35), followed by TVP1 (−0.57), TVP4 (−0.58), and TVP3 (−0.67). TVP algorithm 170 therefore suggests that TVP2 provides the best modulation function 150 to be applied to the patient's tonic stimulation parameters, and thus should be used for the patient going forward. However, TVP algorithm 170 may be repeated from time to time for a patient to see if eventually a better TVP can be determined for the patient. Such re-testing of the patient may be warranted in light of tissue scarring (which can occur up to six months after surgery), migration of the electrode leads in the patient, or to test patients with newer TVPs developed by clinicians over time.

Once a TVP has been selected for a patient after a fitting procedure, it can be desirable to continue to adjust the modulation that the TVP provides in a closed loop fashion. This may be warranted because circumstances may change after the fitting procedure. As just noted, leads can migrate in the patient, or scar tissue can over time cause changes in the efficacy of prescribed stimulation. Further, adjustment to the TVP can be warranted in light of patient posture or activity that is constantly modifying the actual distance between the electrodes and the spinal cord. Breathing and heart rate can also modify this distance. In some patients, these changes can produce changes in the dorsal column activation and in the therapeutic effect of the stimulation for both paresthesia-based therapies that a patient can feel and paresthesia-free therapies that the patient doesn't perceive.

Figure 11:
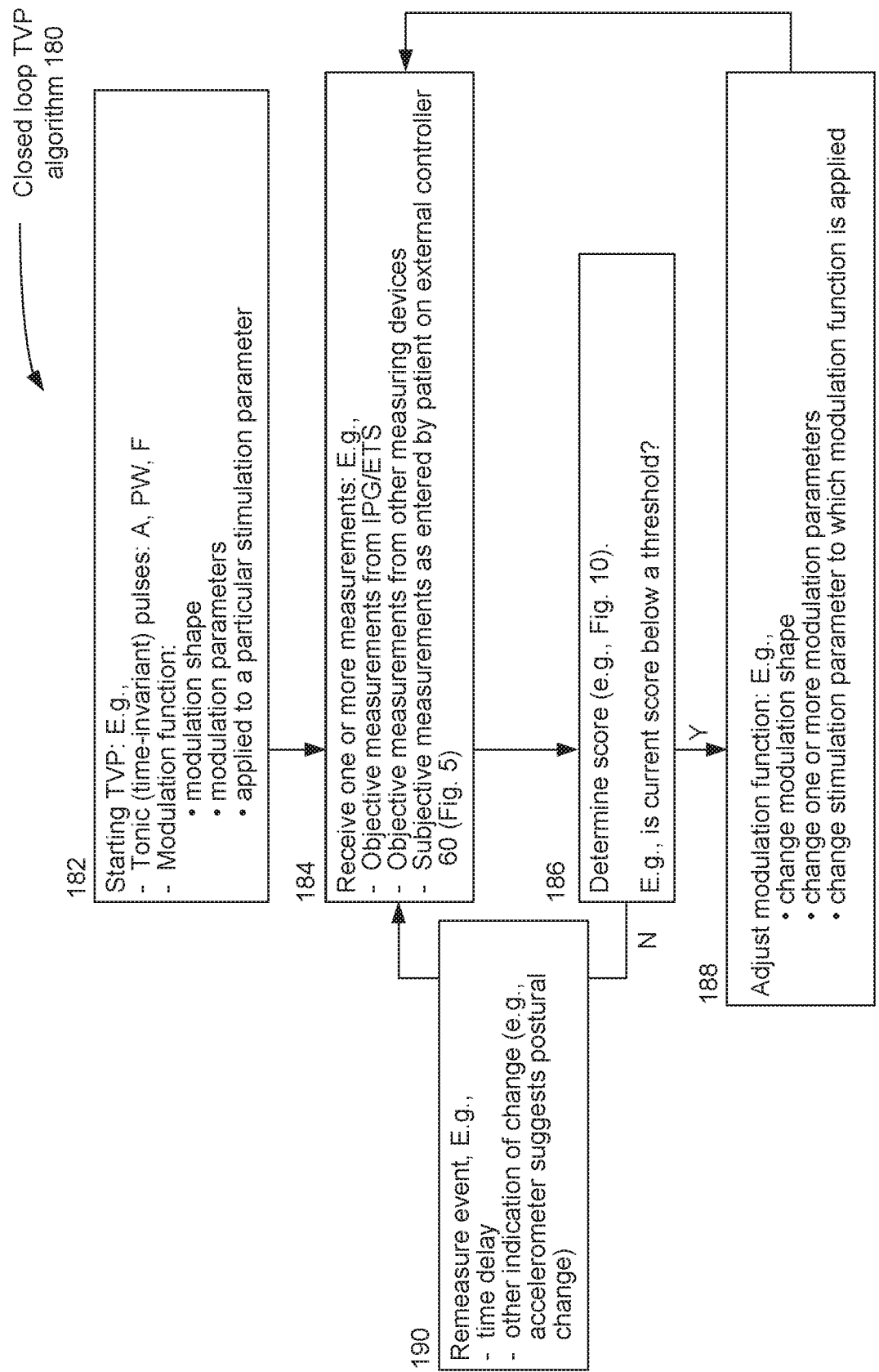
FIG. 11 shows a closed loop TVP algorithm that can be used to adjust a TVP prescribed for the patient.

FIG. 11 shows a closed loop TVP algorithm 180 that can be helpful to adjusting the modulation provided by the prescribed TVP. Due to its closed loop nature, it would be expected that closed loop TVP algorithm 180 would operate as software within the patient's IPG or ETS and executed by the controller circuitry (e.g., 102, FIG. 6A) in such devices. That is, the close loop algorithm 180 may operate without any need to communicate with external devices, such as a clinician program 70 or patient external controller 60 (FIG. 5). That being said, the TVP algorithm 180 operating in the IPG or ETS may also receive input from such external devices or other external sources, as explained further below.

The closed loop TVP algorithm 180 is assumed in step 182 to start with a given TVP for the patient, such as the TVP that was selected as most efficacious for the patient using the TVP algorithm 170 described earlier. Again, it is assumed here (although it is not strictly necessary) that the prescribed TVP is defined by a modulation function 150 that is applied to at least one tonic stimulation parameters A, PW, and F. The modulation function 150 as before would have a particular shape and modulation parameters, and would modulate one or more of the tonic stimulation parameters.

In step 184, and similarly to what was described with respect to TVP algorithm 170, one or more measurements are received by the closed loop TVP algorithm 180. As before, the measurements can comprise one or more objective measurements, and/or one or more subjective measurements, such as those described earlier. In a preferred example, the closed loop TVP algorithm 180 would receive objective measurements. This might be desirable to allow the algorithm 180 to operate automatically without requiring subjective input from the patient. Further, such objective measurements are preferably those taken by the IPG or ETS itself, which again allows for easier operation of the algorithm 180 in the IPG or ETS. That being said, the algorithm 180 can receive objective measurements from other external medical equipment, and such measurements may be for example wirelessly transmitted to the IPG 100 for consideration. Further, the algorithm 180 can also (e.g., wirelessly) receive subjective measurements from the patient. For example, the patient may be able to enter a pain score, a sensation quality ranking, or other qualitative factors or ranking (patient-specific information) into his patient external controller 60, which may in turn be received as subjective measurements by the algorithm 180 in the IPG or ETS. Furthermore, given the ease of communication between the IPG or ETS and the external controller 60, the closed loop TVP algorithm 180 can also operate, at least in part, in the clinician programmer 70 or external controller 60, with TVP adjustments determined by the algorithm 180 being communicated to the IPG or ETS.

In step 186, the algorithm 180 calculates a score for the TVP using the measurement(s) from step 184, similarly to what was described earlier in conjunction with TVP algorithm 170. As noted previously, the score can be determined by, or comprise, a single subjective or objective measurement, such as the ECAP area metrics described earlier. The resulting score can then be assessed by the algorithm at step 186 to see if the TVP is suitably effective or needs adjustment. In this regard, the algorithm 180 can be programmed with at least one threshold, and can determine if the current score for the TVP has gotten worse using that threshold. Assuming that higher scores are indicative of better results, step 186 can inquire whether the current score has dropped below the threshold (or if lower scores are preferred, whether the current score is above the threshold). In another example, two thresholds can be used that define upper and lower desired scores, effectively defining a desired score region between the two thresholds. If the score is too high (above the upper threshold) or too low (below the lower threshold), the algorithm 180 may conclude that the TVP has gotten worse and needs adjustment.

If the score is not worse (e.g., not beyond a threshold) at step 186, the closed loop algorithm 180 can conclude that TVP adjustment is not necessary at this time, and can wait at step 190 until such time as it is necessary to retake further measurements. In one example, step 190 can comprise a time delay, e.g., 10 minutes, which sets the frequency with which the algorithm 180 will take measurements, and potentially make TVP adjustments. Additionally, or alternatively, the algorithm at step 190 can wait for the occurrence of an event that suggests that a change has occurred making it relevant to take further measurements at step 184. In just one example, the algorithm 180 can receive input from the IPG's accelerometer 31 (FIG. 1), which allows the algorithm 180 to determine if the patient has changed posture or is engaging in a particular activity. As noted above, postural or activity changes can affect stimulation therapy, and warrant the need for stimulation adjustments. Algorithm 180 could also receive other inputs indicating a need to take further measurements at step 184.

If the score is worse (e.g., beyond a threshold) at step 186, the algorithm 180 can proceed to step 188 where adjustments to the TVP can be made. In a preferred example, the algorithm 180 at step 188 will adjust an aspect of the modulation function 150, which could comprise changing the shape of modulation, changing one or more modulation parameters, and/or changing the tonic stimulation parameter to which the modulation function 150 is applied (e.g., by applying the modulation function to pulse width instead of amplitude). Rather than adjusting the prescribed modulation function 150 at step 188, an entirely new modulation function could be selected, although this is effectively no different form adjusting the original modulation function. Modulation parameters that can be adjusted at step 188 can comprise the spread of the modulation function (e.g., maximum-minimum) and the middle value of the modulation function (e.g., mid). For example, when the modulation function is applied to the frequency of the tonic stimulation pulses, Fmid (the mean frequency averaged over the period of modulation ($T=1/F_M$), or averaged over a time interval for non-periodic modulation functions), can be adjusted in step 188 in the hope of maintaining the score within a threshold band, below an upper threshold, or above a lower threshold. Alternatively, the frequency spread Fmax-Fmin could be the parameter adjusted in step 188, or any other modulation parameter.

The adjustment the closed loop TVP algorithm 180 makes to the modulation function at step 188 is preferably intelligent. For example, the adjustments made at step 188 may depend on information noticed during the execution of the TVP algorithm 170 during the fitting process, which information may be programmed into the algorithm 180. The adjustment made at step 188 may also depend on, or be constrained by, the originally prescribed modulation function, such that any adjustments are not too radical of a departure from such original function. Once the modulation function is adjusted at step 188, new measurements can again be taken in step 184 to see if the score has improved. If so, the algorithm 180 can wait at step 190, or can proceed to try still further modulation function adjustments in step 188, etc.

In another embodiment, the threshold(s) used in step 186 may be automatically updated based on long term values of the measurement(s) used to determine the score. For example, if the ECAP area is the only feature used in determining the score, it can be averaged over a short time window spanning between 1 and 5 consecutive modulation periods (e.g., 1 to 5 $T=1/F_M$), while the threshold for the score can be averaged over a longer time window spanning minutes, or hours, or days (e.g., >5 T). This enables the algorithm 180 to adapt to changes due to disease progression in the patient, the development of scar tissue, and lead migration.

Various aspects of the disclosed techniques, including processes implementable in the IPG or ETS or in external devices such as the clinician programmer or external controller, such as GUI 160, TVP algorithm 170 and closed loop TVP algorithm 180, can be formulated and stored as instructions in a computer-readable media associated with such devices, such as in a magnetic, optical, or solid state memory. The computer-readable media with such stored instructions may also comprise a device readable by the clinician programmer or external controller, such as in a memory stick or a removable disk, and may reside elsewhere. For example, the computer-readable media may be associated with a server or any other computer device, thus allowing instructions to be downloaded to the clinician programmer system or external controller or to the IPG or ETS, via the Internet for example.

Although particular embodiments of the present invention have been shown and described, the above discussion is not intended to limit the present invention to these embodiments. It will be obvious to those skilled in the art that various changes and modifications may be made without departing from the spirit and scope of the present invention. Thus, the present invention is intended to cover alternatives, modifications, and equivalents that may fall within the spirit and scope of the present invention as defined by the claims.

What is claimed is:

1. A method for determining stimulation for a patient having an implantable stimulator device, comprising:
    (a) applying different modulation functions to time-invariant pulse parameters to create a plurality of different time-varying pulse waveforms, wherein each of the modulation functions modulates at least one of the time-invariant pulse parameters;
    (b) applying each of the time-varying pulse waveforms to the patient via the implantable stimulator device;
    (c) obtaining at least one measurement of a neural response evoked by recruitment of neural fibers in the patient's tissue in response to each of the applied time-varying pulse waveforms; and
    (d) selecting one or more of the time-varying pulse waveforms for the patient based at least in part on the at least one measurements.

2. The method of claim 1, further comprising as an initial step determining the time-invariant pulse parameters for use with the patient.

3. The method of claim 1, wherein the at least one measurement obtained for each of the applied time-varying pulse waveforms is indicative of the effectiveness of that time-varying pulse waveform for the patient.

4. The method of claim 1, wherein the time-invariant pulse parameters comprise a pulse amplitude, a pulse width, and a pulse frequency.

5. The method of claim 1, wherein each of the modulation functions is periodic to periodically modulate the at least one of the time-invariant pulse parameters.

6. The method of claim 1, wherein at least one of the modulation functions is non-periodic, wherein the at least one non-periodic function arbitrarily modulates the at least one of the time-invariant pulse parameters.

7. The method of claim 1, wherein the at least one measurement is obtained using the implantable stimulator device.

8. The method of claim 7, wherein the at least one measurement comprises at least one feature derived from of an electrospinogram (ESG) signal sensed at the implantable stimulator device.

9. The method of claim 7, wherein the at least one measurement comprises at least one feature derived from one or more evoked compound action potentials sensed at the implantable stimulator device.

10. The method of claim 1, wherein the at least one measurement is obtained using a system separate from the implantable stimulator device.

11. The method of claim 1, wherein the at least one measurement for each of the applied time-varying pulse waveforms further comprises a subjective measurement determined based on feedback from the patient.

12. The method of claim 11, wherein the at least one subjective measurement comprises a rating provided from the patient relevant to a symptom of the patient.

13. The method of claim 11, wherein the at least one subjective measurement comprises a stimulation threshold indicative of a strength of stimulation perceived by the patient.

14. The method of claim 1, wherein step (d) comprises
    determining a score for each of the applied time-varying pulse waveforms using the at least one measurement obtained for that time-varying pulse waveform, and
    selecting the one or more of the time-varying pulse waveforms for the patient using the determined scores.

15. The method of claim 14, wherein a plurality of measurements are obtained for each of the applied time-varying pulse waveforms, wherein each of the plurality of measurements are weighted when determining the score for each of the applied time-varying pulse waveforms.

16. The method of claim 1, wherein the method uses an external device in communication with the implantable stimulator device.

17. The method of claim 16, wherein step (a) is performed using the external device.

18. The method of claim 16, wherein the at least one measurement for each of the applied time-varying pulse waveforms is received at the external device, and wherein step (d) is performed using the external device.

19. The method of claim 16, further comprising (e) using the external device to program the implantable stimulator device with the selected one or more of the time-varying pulse waveforms.

* * * * *